United States Patent
Sugiyama

(10) Patent No.: US 11,555,814 B2
(45) Date of Patent: *Jan. 17, 2023

(54) METHOD FOR ACTIVATION OF HELPER T CELL AND COMPOSITION FOR USE IN THE METHOD

(71) Applicant: International Institute of Cancer Immunology, Inc., Osaka (JP)

(72) Inventor: Haruo Sugiyama, Minoo (JP)

(73) Assignee: International Institute of Cancer Immunology, Inc., Osaka (JP)

(*) Notice: Subject to any disclaimer, the term of this patent is extended or adjusted under 35 U.S.C. 154(b) by 534 days.

This patent is subject to a terminal disclaimer.

(21) Appl. No.: 16/163,682

(22) Filed: Oct. 18, 2018

(65) Prior Publication Data

US 2020/0064332 A1 Feb. 27, 2020

Related U.S. Application Data

(62) Division of application No. 12/449,765, filed as application No. PCT/JP2008/053417 on Feb. 27, 2008, now Pat. No. 10,139,395.

(30) Foreign Application Priority Data

Feb. 27, 2007 (JP) ................................ 2007-047317

(51) Int. Cl.
G01N 33/50 (2006.01)
A61K 39/00 (2006.01)
C07K 14/47 (2006.01)
A61K 38/00 (2006.01)

(52) U.S. Cl.
CPC .... *G01N 33/505* (2013.01); *A61K 39/001153* (2018.08); *C07K 14/4748* (2013.01); *A61K 38/00* (2013.01); *A61K 2039/55516* (2013.01)

(58) Field of Classification Search
None
See application file for complete search history.

(56) References Cited

U.S. PATENT DOCUMENTS

| 7,030,212 | B1 | 4/2006 | Sugiyama et al. |
| 7,063,854 | B1 | 6/2006 | Gaiger et al. |
| 7,342,092 | B2 | 3/2008 | Sugiyama |
| 7,378,384 | B2 | 5/2008 | Sugiyama et al. |
| 7,390,871 | B2 | 6/2008 | Sugiyama et al. |
| 7,420,034 | B2 | 9/2008 | Sugiyama et al. |
| 7,517,950 | B2 | 4/2009 | Sugiyama et al. |
| 7,608,685 | B1 | 10/2009 | Sugiyama et al. |
| 7,622,119 | B2 | 11/2009 | Sugiyama |
| 7,666,985 | B2 | 2/2010 | Sugiyama et al. |
| 7,939,627 | B2 | 5/2011 | Nishihara et al. |
| 8,105,604 | B2 | 1/2012 | Sugiyama |
| 8,388,975 | B2 | 3/2013 | Sugiyama |
| 8,765,687 | B2 | 7/2014 | Scheinberg et al. |
| 9,233,149 | B2 | 1/2016 | Scheinberg et al. |
| 9,833,493 | B2 | 12/2017 | Kubo et al. |
| 10,124,046 | B2 | 11/2018 | Sugiyama |
| 10,654,892 | B2 * | 5/2020 | Sugiyama ............... A61P 37/04 |
| 10,759,840 | B2 * | 9/2020 | Sugiyama ............... A61P 11/00 |
| 2002/0128196 | A1 | 9/2002 | Call et al. |
| 2004/0097703 | A1 | 5/2004 | Sugiyama |
| 2004/0247609 | A1 | 12/2004 | Sugiyama |
| 2005/0002951 | A1 | 1/2005 | Sugiyama et al. |
| 2006/0121046 | A1 | 6/2006 | Gaiger et al. |
| 2006/0165708 | A1 | 7/2006 | Mayumi et al. |
| 2006/0217297 | A1 | 9/2006 | Sugiyama et al. |
| 2007/0082860 | A1 | 4/2007 | Sugiyama et al. |
| 2007/0128207 | A1 | 6/2007 | Sugiyama |
| 2008/0070835 | A1 | 3/2008 | Sugiyama |
| 2008/0152631 | A1 | 6/2008 | Sugiyama |
| 2009/0099090 | A1 | 4/2009 | Sugiyama et al. |
| 2009/0143291 | A1 | 6/2009 | Sugiyama et al. |
| 2009/0263409 | A1 | 10/2009 | Sugiyama |
| 2009/0281043 | A1 | 11/2009 | Sugiyama et al. |
| 2010/0062013 | A1 | 3/2010 | Sugiyama |
| 2010/0092522 | A1 | 4/2010 | Scheinberg |
| 2010/0190163 | A1 | 7/2010 | Sugiyama |

(Continued)

FOREIGN PATENT DOCUMENTS

| CA | 2544214 A1 * | 5/2005 |
| CN | 1671733 A | 9/2005 |

(Continued)

OTHER PUBLICATIONS

Fujiki et al (J. Immunotherapy, Apr. 2007, 30(3): 282-293) (Year: 2007).*
CA accession No. 2005: 429563 (2004) (Year: 2004).*
Lipski et al (J. Neuroinflamm. 2017, 14: 136, pp. 1-22) (Year: 2017).*
Fumihiro Fujiki et al, "A WT1 protein-derived, naturally processed 16-mer peptide, WT1[332], is a promiscuous helper peptide for induction of WT1-specific Th1-type CD4+ T cells," Microbiol Immunology Dec. 12, 2008, vol. 52, No. 12, pp. 591-600, XP-002590600.
Supplementary European Search Report dated Jul. 20, 2010 issued in corresponding European Patent Application No. 08712039.0-2404.

(Continued)

Primary Examiner — Michael Szperka
Assistant Examiner — Marianne DiBrino
(74) Attorney, Agent, or Firm — Finnegan, Henderson, Farabow, Garrett & Dunner, LLP

(57) ABSTRACT

Disclosed are: a method for activating a helper T cell, which comprises the step of adding a WT1 peptide to an antigen-presenting cell to activate the helper T cell, wherein the WT1 peptide is capable of binding to any one selected from an HLA-DRB1*1501 molecule, an HLA-DPB1*0901 molecule and an HLA-DPB1*0501 molecule; a composition for use in the method; a therapeutic and/or prophylactic method for cancer by activating a helper T cell; a pharmaceutical composition for use in the therapeutic and/or prophylactic method; and others.

2 Claims, 5 Drawing Sheets

Specification includes a Sequence Listing.

(56) References Cited

U.S. PATENT DOCUMENTS

| | | |
|---|---|---|
| 2010/0247556 A1 | 9/2010 | Sugiyama |
| 2010/0292160 A1 | 11/2010 | Sugiyama |
| 2011/0098233 A1 | 4/2011 | Sugiyama |
| 2012/0045465 A1 | 2/2012 | Sugiyama |
| 2012/0195918 A1 | 8/2012 | Sugiyama |
| 2013/0196427 A1 | 8/2013 | Sugiyama |
| 2013/0243800 A1 | 9/2013 | Sugiyama |
| 2013/0266958 A1 | 10/2013 | Sugiyama et al. |
| 2015/0328278 A1 | 11/2015 | Kubo et al. |
| 2018/0207254 A1 | 7/2018 | Sugiyama |

FOREIGN PATENT DOCUMENTS

| | | |
|---|---|---|
| CN | 1902313 A | 1/2007 |
| EP | 1 696 027 A1 | 8/2006 |
| EP | 2 098 595 A1 | 9/2009 |
| JP | 2002-525099 A | 8/2002 |
| JP | 2006-280324 A | 10/2006 |
| WO | WO 00/18795 A1 | 4/2000 |
| WO | WO 01/62920 A2 | 8/2001 |
| WO | WO 02/099084 A2 | 12/2002 |
| WO | WO 03/002142 A1 | 1/2003 |
| WO | WO 03/028758 A1 | 4/2003 |
| WO | WO 03/037060 A2 | 5/2003 |
| WO | WO 03/106682 A1 | 12/2003 |
| WO | WO 2005/045027 A1 | 5/2005 |
| WO | WO2005045027 A1 * | 5/2005 |
| WO | WO 2005/095598 A1 | 10/2005 |
| WO | WO 2007/097358 A1 | 8/2007 |
| WO | WO 2008/081701 A1 | 7/2008 |
| WO | WO 2008/105462 A1 | 9/2008 |
| WO | WO 2010/123065 A1 | 10/2010 |
| WO | WO 2012/046730 A1 | 4/2012 |

OTHER PUBLICATIONS

Daniel A. Haber et al., "An internal Deletion within an 11p13 Zinc Finger Gene Contributes to the Development of Wilms'Tumor," Cell. 1990, vol. 61 pp. 1257-1269.

Katherine M. Call et al., "Isolation and Characterization of a Zinc Finger Polypeptide Gene at the Human Chromosome 11 Wilms' Tumor Locus," Cell, 1990, vol. 60, pp. 509-520.

A. L. Menke et al., "The Wilms' Tumor 1 Gene: Oncogene or Tumor Suppressor Gene?," International Review of Cytology, 1998, vol. 181, pp. 151-212.

Tamotsu Yamagami et al., "Growth Inhibition of Human Leukemic Cells by WT1 (Wilms Tumor Gene) Antisense Oligodeoxynucleotides: Implications for the Involvement of WT1 in Leukemogenesis," Blood, 1996, vol. 87, No. 7, pp. 2878-2884.

Kazushi Inoue et al., "Wilms' Tumor Gene (WT1) Competes With Differentiation-Inducing Signal in Hematopoetic Progenitor Cells," Blood, 1998, vol. 91, No. 8, pp. 2969-2976.

Akihiro Tsuboi et al., :Constitutive expression of the Wilms' tumor gene WT1 inhibits the differentiation of myeloid progenitor cells by promotes their proliferation in response to granulocyte-colony stimulating factor (G-CSF), Leukemia Research, 1999, vol. 23, pp. 499-505.

Yoshihiro Oka et al., "Human cytotoxic T-lymphocyte responses specific for peptides of the wild-type Wilms'tumor gene (WT1) product,"Immunogenetics (2000), No. 51, pp. 99-107.

Feng Guang et al., Antigen-specific CD4+ T-Cell Help is Required to Activate a Memory CD8+ T Cell to a Fully Functional Tumor Killer Cell[1], Cancel Research, 2002, vol. 62, pp. 6438-6441.

Gang Zeng, "MHC Class II-Restricted Tumor Antigens Recognized by CD4+ T Cells: New Strategies for Cancer Vaccine Design," Journal of Immunotherapy, 2001, vol. 24, No. 3, pp. 195-204.

Ashley John Knights, "Prediction of an HLA-DR-binding peptide derived from Wilms' tumor 1 protein and demonstration in vitro immunogenicity of WT1(124-138)-pulsed dendritic cells generated according to anoptimized protocol," Cancert Immunol Immunother, 2002, vol. 51, pp. 271-281.

R. Sotiriadou et al., "Peptide HER2(776-788) represents a naturally processed broad MHC class II-restricted T cell epitope," British Journal of Cancer (2001), vol. 85, No. 10, pp. 1527-1534.

John A. Hural et al., Identification of Naturally Processed CD4 T Cell Epitopes from the Prostate-Specific Antigen Kallikrein 4 Using Peptide-Based in Vitro Stimulation, The Journal of Immunology, 2000, vol. 169, No. 1, pp. 557-565.

Office Action dated May 5, 2011, issued in corresponding Chinese Application No. 2008/80006096.5.

Examination Report dated Sep. 23, 2011, issued in corresponding New Zealand Application No. 578721.

Office Action dated Aug. 21, 2011, issued in corresponding Israeli Application No. 200,161.

Office Action dated Nov. 8, 2011, issued in corresponding Chinese Application No. 2008/80006096.5.

Sachiko Futami et al., "HLA-DRB1*1502 Allele, Subtype of DR15, is Associated with Susceptibility to Ulcerative Colitis and its Progression," Digestive Diseases and Sciences, vol. 40, No. 4 (Apr. 1995), pp. 814-818.

Office Action dated Nov. 29, 2011, issued in corresponding Ukrainian Application No. 2009/09812.

Office Action dated Jan. 9, 2012, issued in corresponding New Zealand Application No. 578721.

Fujiki et al., J. Immunother, 2007, 30(3): 282-293.

Marchand et al., Int. J. Cancer 80: 219-230, 1999.

Bodey et al., Anticancer Research 20: 2665-2676, 2000.

Gao et al., J. Immunother, 23: 643-653, 2000.

Marchand et al., Exp. Opin. Biol. Ther. 1(3): 497-510, 2001.

Celis, J. Clin. Invest. 2002, 110, 12: 1765-1768.

A_GENSEQ AEA 15677, Jul. 28, 2005.

Office Action dated Feb. 24, 2012, issued in corresponding European Application No. 08 712 039.0-2404.

Office Action dated Mar. 2, 2012, issued in corresponding Ukrainian Patent Application No. 2009/09812.

Third Office Action dated Mar. 28, 2012, issued in corresponding Chinese Patent Application No. 2008/8000609.5.

English summary dated Jun. 21, 2012, of Office Action issued in corresponding Mexican Patent Application No. MX/a/2009/009168.

Office Action dated Jun. 15, 2012, issued in corresponding Russian Patent Application No. 2009/135802.

Office Action received Dec. 12, 2012, issued in Russian Patent Application No. 2009/135802/10.

English translation of Office Action dated Jun. 15, 2012, issued in corresponding Russian Patent Application No. 2009/135802 (9 pages).

Office Action issued in Russian Patent Application No. 2009/135802.

Marsh et al., "The HLA Facts Book," Academic Press, England (2000), pp. 299 and 377 (4 pages, including cover and copyright pages).

Fournier and Schirrmacher, Expert. Rev. Vaccines 8(1); 51-66, 2009.

Schrieber et al., Seminar. Immunol. 22: 105-112, 2010.

Klebanoff et al., Immunol. Rev. 2011, 239: 27-44.

Office Action dated Sep. 25, 2012, issued in Japanese Patent Application No. 2009-501276.

Office Action dated May 28, 2013, issued in Vietnamese Patent Application No. 1-2009-01834.

Office Action dated May 28, 2013, issued in Colombian Patent Application No. 09103858.

English Translation of Office Action dated Nov. 29, 2013, issued in Chinese Patent Application No. 2013/10009095.9.

Office Action with search report dated Jun. 26, 2014, issued in Chinese Patent Application No. 2013/0058504.4.

Freshney, Culture of Animal Cells, A Manual of Basic Technique, Alan R. Liss, Inc., 1983, New York, p. 4.

Dermer, Bio/Technology, 1994, 12:320.

Summons to attend oral proceedings, issued in European Patent Application No. 08712039.0, dated Oct. 23, 2014 (6 pages).

Reexamination Decision, dated Feb. 17, 2015, issued in Chinese Patent Application No. 2008/80006096.5.

Office Action dated Sep. 7, 2015, issued in Chinese Patent Application No. 2013/0058504, 4 pages.

(56) References Cited

OTHER PUBLICATIONS

Final Office Action dated Jun. 11, 2018, issued in U.S. Appl. No. 13/877,768, 25 pages.
Dibrino, Marianne et al., "HLA-A1 and HLA-A3 T Cell Epitopes Derived from Influenza Virus Proteins Predicted from Peptide Binding Motifs," *The Journal of Immunology*, vol. 151, pp. 5930-5935 (1993).
Celis, Esteban et al., "Identification of Potential CTL Epitopes of Tumor-Associated Antigen MAGE-1 for Five Common HLA-A Alleles," *Molecular Immunology*, vol. 31, No. 18, pp. 1423-1430 (1994).
Office Action dated Feb. 26, 2018, issued by the Mexican Patent Office in corresponding Mexican Patent Application No. MX/a/2013/003884 (4 pages).
Office Action dated Jan. 24, 2018, issued by the Russian Patent Office in corresponding Russian Patent Application No. 2014/104572/10 (9 pages).
Lee, Kang-Hun et al., "Increased Vaccine-Specific T Cell Frequency After Peptide-Based Vaccination Correlates with Increased Susceptibility to In Vitro Stimulation, But Does Not Lead to Tumor Regression", from *The Journal of Immunology*, dated Dec. 1, 1999, 163 (11) pp. 6292-6300.
Colombian Patent Application No. 15162173: Office Action, dated Sep. 6, 2016, with partial English Translation (16 pages).
Eurasian Patent Application No. 2015/91168: Office Action, dated Dec. 5, 2016, with English Translation (1 page).
Hohler et al., "HLA-DRB1*1301 and 1302 protect against chronic hepatitis B," *Journal of Hepatology*, 26: 503-507(1997).
U.S. Appl. No. 14/652,298, filed Jun. 15, 2015, by Kubo: Non-Final Office Action, dated Dec. 30, 2016, with Notice of References Cited (PTO-892) (21 pages).
Kobayashi, H. et al., (2006) "Defining MHC class II T helper epitopes for WT1 tumor antigen," *Cancer Immunol Immunother*, 55:850-860 (11 pages).
U.S. Appl. No. 14/652,298, filed Jun. 15, 2015, by Kubo: Requirement for Restriction/Election, dated Aug. 9, 2016, with Notice of References Cited (PTO-892) (10 pages).
Altomonte, M. et al. (2003) "Targeted therapy of solid malignancies via HLA class II antigens: a new biotherapeutic approach?": *Oncogene*, 22:6564-6569.
Australia Patent Application No. 20113/13327, by International Institute of Cancer Immunology, Inc. et al.: Patent Examination Report No. 1, issued Jun. 2, 2014 (5 pages).
Bardi, M.S. et al. (2012) "HLA-A, B and DRB1 allele and haplotype frequencies in volunteer bone marrow donors from the north of Parana State," *Rev. Bras. Hematol. Hemoter.*, 34(1):25-30.
Canadian Patent Application No. 2,677,075, by International Institute of Cancer Immunology, Inc.: Office Action, dated May 14, 2014 (3 pages).
Chinese Patent Application No. 2011/80058552.2, filed Oct. 4, 2011, by International Institute of Cancer Immunology, Inc.: First Office Action, dated Apr. 9, 2014, with English translation (15 pages).
Chinese Patent Application No. 2013/10009095.9, filed Feb. 27, 2008, by International Institute of Cancer Immunology, Inc..: Second Office Action, dated Jul. 31, 2014, with English translation (9 pages).
Dengjel, J. et al. (2006) "Unexpected Abundance of HLA Class II Presented Peptides in Primary Renal Cell Carcinomas," *Clin. Cancer Res.*, 12:4163-4170.
European Patent Application No. 11830662.0, by International Institute of Cancer Immunology, Inc., et al.: Examination Report (Communication pursuant to Article 94(3) EPC), dated Jun. 23, 2015 (3 pages).
Fujiki, F. et al. (2004) "Identification of HLA-class II restricted WT1 peptide which can induce WT1 specific CD4+ helper T cells," *Proceedings of the Japanese Society for Immunology*, 34:210, Abstract 2-G-W29-08-O/P, Japanese with English translation.
Fujiki, F. et al. (2005) "Identification of WT1 peptide which can induce WT1 specific CD4+ helper T cells in an HLA-class II-restricted manner and examination of the usefulness of the peptide," *Proceedings of the Japanese Society for Immunology*, 35:187, Abstract 2-F-W27-8-O/P, Japanese with English translation.
Gao, F.G. et al. (Nov. 2002) "Antigen-specific CD4+ T-Cell Help is Required to Activate a Memory CD8+ T Cell to a Fully Functional Tumor Killer Cell" *Cancer Research*, 62:6438-6441.
Han, F. et al. (2012) "HLA-DQ association and allele competition in Chinese narcolepsy" *Tissue Antigens*, 80:328-335.
Hansen, P.W. et al. (1987) "Cytotoxic Human HLA Class II Restricted Purified Protein Derivative-Reactive T-Lymphocyte Clones" *Scan. J. Immunol.*, 25:295-303.
House, K.D. et al. (2012) "The search for a missing HLA-DRB1*09 Allele" 38th Annual Meeting of the American Society for Histocompatibility and Immunogenetics, Oct. 8-12, 2012, San Juan, Puerto Rico. *Abstracts/Human Immunology*, 73:20, Abstract 23-OR.
International Patent Application No. PCT/JP2011/072874, filed Oct. 4, 2011, by International Institute of Cancer Immunology, Inc et al.: International Search Report, dated Dec. 20, 2011 (3 pages).
International Patent Application No. PCT/JP2011/072874, filed Oct. 4, 2011, by International Institute of Cancer Immunology, Inc. et al.: International Preliminary Report on Patentability, including Notification of Transmittal, dated May 16, 2013 (10 pages).
International Patent Application No. PCT/JP2013/083580, filed Dec. 16, 2013, by Otsuka Pharmaceutical Co., Ltd. et al.: International Search Report, dated Feb. 25, 2014 (5 pages).
International Patent Application No. PCT/JP2013/083580, filed Dec. 16, 2013, by Otsuka Pharmaceutical Co., Ltd. et al.: International Preliminary Report on Patentability, including Notification of Transmittal, dated Jul. 2, 2015 (9 pages).
Irie, A. et al. (Aug. 2012) "Establishment of HLA-DR4 transgenic mice having antigen-presenting function to HLA-DR4-restricted CD4+ Th cell" *MHC (Major Histocompatibility Complex). Official Journal of the Japanese Society for Histocompatibility and Immunogenetics*, 19(2):94, Abstract O-36 (p. 80). Japanese with English translation.
Katsuhara, A. et al. (2015) "Transduction of a Novel HLA-DRB1*04:05-restricted, WT1-specific TCR Gene into Human CD4+ T Cells Confers Killing Activity Against Human Leukemia Cells" *Anticancer Research*, 35:1251-1262.
Knutson, K.L. and M.L. Disis (2005) "Tumor antigen-specific T helper cells in cancer immunity and immunotherapy" *Cancer Immunol. Immunother.*, 54:721-728.
Lehe, C. et al. (Aug. 2008) "The Wilms' Tumor Antigen is a Novel Target for Human CD4+ Regulatory T Cells: Implications for Immunotherapy" *Cancer Res.*, 68(15):6350-6359.
Lin, Y. et al. (Apr. 2013) "HLA-DPB1*05:01-restricted WT1$_{332}$-specific TCR-transduced CD4+ T Lymphocytes Display a Helper Activity for WT1-specific CTL Induction and a Cytotoxicity Against Leukemia Cells" *J. Immunother.*, 36(3):159-170.
Master, P.S. et al. (1991) "Patterns of Membrane Antigen Expression by AML Blasts: Quantitation and Histogram Analysis" *Leukemia and Lymphoma*, 5:317-325.
May, R.J. et al. (Aug. 2007) "Peptide Epitopes from the Wilms' Tumor 1 Oncoprotein Stimulate CD4+ and CD8+ T Cells That Recognize and Kill Human Malignant Mesothelioma Tumor Cells" *Clin. Cancer Res.*, 13(15):4547-4555.
Megiorni, F. and A. Pizzuti (2012) "HLA-DQA1 and HLA-DQB1 in Celiac disease predisposition: practical implications of the HLA molecular typing" *J. Biomed. Sci.*, 19:88 (5 pages).
Müller, L. et al. (2003) "Synthetic peptides derived from the Wilms' tumor 1 protein sensitize human T lymphocytes to recognize chronic myelogenous leukemia cells" *Hematol. J.*, 4:57-66.
Mustafa, A.S. and T. Godal (1987) "BCG induced CD4+ cytotoxic T cells from BCG vaccinated healthy subjects: relation between cytotoxicity and suppression in vitro" *Clin. Exp. Immunol.*, 69:255-262.
Pakistan Patent Application No. 720/2011, by Osaka University and Otsuka Pharmaceutical Co., Ltd.: Examination Report, dated Jan. 10, 2013 (2 pages).
Rezvani, K. et al. (2005) "T-Cell Responses Directed against Multiple HLA-A*0201-Restricted Epitopes Derived from Wilms'

(56) References Cited

OTHER PUBLICATIONS

Tumor 1 Protein in Patients with Leukemia and Healthy Donors: Identification, Quantification, and Characterization" *Clin. Cancer Res.*, 11:8799-8807.
Sogo, Shinji, Study Director, Otsuka Pharmaceutical Co. Ltd. "Final Study Report: Effect of OVT-101 on the Helper-activity Against WT1-specific CTL From Human Peripheral Blood Mononuclear Cells" Study No. 030697, Report No. 025539; completed on Dec. 9, 2010 (22 pages).
Sogo, Shinji, Study Director, Otsuka Pharmaceutical Co. Ltd. "Final Study Report: Cytolytic Activity of OCV-501-Specific Th1 Clones" Study No. 035171, Report No. 028745; completed on Mar. 15, 2013 (39 pages).
Yazawa, T. et al. (1999) "Lack of class II transactivator causes severe deficiency of HLA-DR expression in small cell lung cancer" *J. Pathol.*, 187:191-199.
Bruening, W. et al. (May 1992) "Germline intronic and exonic mutations in the Wilms'tumour gene (WT1) affecting urogenital development" *Nature Genetics*, 1:144-148.
Database GenBank Accession No. AAC60604.1 (Jul. 23, 1993) "Wilms' tumor suppressor, partial [*Homo sapiens*]" [online]. National Center for Biotechnology Information (NCBI), U.S. National Library of Medicine; http://www.ncbi.nlm.nih.gov/protein/AAC60604; retrieved on Feb. 15, 2016 (1 page).
Database GENESEQ Accession No. ABG52313 (Feb. 25, 2003) "Human liver peptide, SEQ ID No. 30961" [online]. Retrieved from EBI on Apr. 26, 2009, Accession No. GSN:ABG52313 (1 page).
Database GENESEQ Accession No. AAG78443 (Jun. 15, 2007) "WT33 Wilm's tumour protein" [online]. Retrieved from EBI on Apr. 27, 2009, Accession No. GSP:AAG78443 (2 pages).
Database GENESEQ Accession No. AAG78450 (Apr. 12, 2002) "WT33 protein fragment sequence # 1" [online]. Retrieved from EBI on Apr. 27, 2009, Accession No. GSN:AAG78450 (1 page).
Database JPO Proteins Accession No. BD589960 (Jul. 17, 2003) "Cancer vaccine comprising cationic liposome and cancer antigen based on tumor suppressor gene WT1" [online]. Retrieved from EBI on Mar. 17, 2008, Accession No. JPOP:BD589960 (1 page).
Database JPO Proteins Accession No. BD619917 (Jul. 17, 2003) "Compositions and methods for WT1 specific immunotherapy" [online]. Retrieved from EBI on Mar. 17, 2008, Accession No. JPOP:BD619917 (1 page).
European Patent Application No. 13864968.6, filed Dec. 16, 2013, by Otsuka Pharmaceutical Co., Ltd. et al.: Extended European Search Report and Search Opinion, dated Jun. 6, 2016 (7 pages).
Friede, T. et al. (1996) "Natural ligand motifs of closely related HLA-DR4 molecules predict features of rheumatoid arthritis associated peptides" *Biochim Biophys Acta*, 1316(2):85-101.
Gessler, M. et al. (Feb. 22, 1990) "Homozygous deletion in Wilms tumours of a zinc-finger gene identified by chromosome jumping" *Nature*, 343:774-778.
Healthline Networks, Inc. (2008) "Non-Hodgkin's Lymphoma: In Depth-Overview" [online]. Retrieved from the Internet: healthline.com/channel/non-hodgkins-lymphoma_indepth-overview, on Dec. 2, 2008 (3 pages).
Ishioka, G.Y. et al. (1999) "Utilization of MHC class I transgenic mice for development of minigene DNA vaccines encoding multiple HLA-restricted CTL epitopes" *J Immunol*, 162(7):3915-3925.
Janeway, C.A. et al. "Chapter 3: Antigen Recognition by B-cell and T-cell Receptors" in *Immunobiology*, 5th Ed. New York: Garland Science, 2001; pp. 116-117.
Kim, J-H. et al. (2000) "In vitro binding analysis of hepatitis B virus preS-derived putative helper T-cell epitopes to MHC class II molecules using stable HLA-DRB1 *0405/-DRA*0101 transfected cells" *IUBMB Life*, 50:379-384.
Maffei, A. and P.E. Harris (1998) "Peptides Bound to Major Histocompatibility Complex Molecules" *Peptides*, 19(1):179-198.
Maslak, P.G. et al. (2010) "Vaccination with synthetic analog peptides derived from WT1 oncoprotein induces T-cell responses in patients with complete remission from acute myeloid leukemia" *Blood*, 116(2):171-179.
May, R.J. et al. (2006) "CD4+ peptide epitopes from the WT1 oncoprotein stimulate CD4+ and CD8+ T cells that recognize and kill leukemia and solid tumor cells" *Blood* (*ASH Annual Meeting Abstracts*), 108(11 Part 1):1058A, Abstract 3706. 48th Annual Meeting of the American-Society of Hematology; Orlando, FL, USA; Dec. 9-12, 2006.
Naylor, P.H. et al. (2011) "Peptide Based Vaccine Approaches for Cancer—A Novel Approach Using a WT-1 Synthetic Long Peptide and the IRX-2 Immunomodulatory Regimen" *Cancers*, 3(4):3991-4009.
Özdemir, E. et al. (Feb. 15, 1997) "HLA-DRB1*0101 and *0405 as protective alleles in Japanese patients with renal cell carcinoma" *Cancer Research*, 57(4):742-746.
Rammensee, H.G. et al. (1995) "MHC ligands and peptide motifs: first listing" Immunogenetics, 41(4):178-228.
Singh, H. and G.P.S. Raghava (2001) "ProPred: prediction of HLA-DR binding sites" *Bioinformatics*, 17(12):1236-1237.
Slingluff, C.L. et al. (Oct. 2001) "Phase I trial of a melanoma vaccine with gp100$_{280-288}$ peptide and tetanus helper peptide in adjuvant: immunologic and clinical outcomes" *Clinical Cancer Research*, 7(10):3012-3024.
Sugiyama, H. (2002) "Cancer Immunotherapy Targeting WT1 Protein" *Int J Hematol*, 76(2):127-132.
Tangri, S. et al. (2001) "Structural features of peptide analogs of human histocompatibility leukocyte antigen class I epitopes that are more potent and immunogenic than wild-type peptide" *J Exp Med*, 194(6):833-846.
Tsuboi, A. et al. (Dec. 2002) "Enhanced induction of human WT1-specific cytotoxic T lymphocytes with a 9-mer WTI peptide modified at HLA-A*2402-binding residues" *Cancer Immunol Immunother*, 51(11-12):614-620.
U.S. Appl. No. 10/578,183, filed Feb. 26, 2007, by Sugiyama: Non-Final Rejection, dated Apr. 26, 2010.
U.S. Appl. No. 10/578,183, filed Feb. 26, 2007, by Sugiyama: Miscellaneous Office Action, dated Dec. 8, 2010.
U.S. Appl. No. 10/578,183, filed Feb. 26, 2007, by Sugiyama: Final Rejection, dated Oct. 12, 2011.
U.S. Appl. No. 10/578,183, filed Feb. 26, 2007, by Sugiyama: Final Rejection, dated May 24, 2012.
U.S. Appl. No. 10/578,183, filed Feb. 26, 2007, by Sugiyama: Non-Final Rejection, dated Mar. 11, 2015.
U.S. Appl. No. 10/578,183, filed Feb. 26, 2007, by Sugiyama: Final Rejection, dated Dec. 11, 2015.
U.S. Appl. No. 13/755,185, filed Jan. 31, 2013, by Sugiyama: Non-Final Rejection, dated Mar. 7, 2014.
U.S. Appl. No. 13/755,185, filed Jan. 31, 2013, by Sugiyama: Final Rejection, dated Sep. 25, 2014.
U.S. Appl. No. 13/755,185, filed Jan. 31, 2013, by Sugiyama: Advisory Action, dated Feb. 5, 2015.
U.S. Appl. No. 13/877,768, filed Jun. 21, 2013, by Sugiyama: Non-Final Rejection, dated Jun. 2, 2016.
Wymann, D. et al. (1999) "Human B cells secrete migration inhibition factor (MIF) and present a naturally processed MIF peptide on HLA-DRB1*0405 by a FXXL motif" *Immunology*, 96(1):1-9.
Yatsuda, J. et al. (Dec. 2013) "Establishment of HLA-DR4 Transgenic Mice for the Identification of CD4+ T Cell Epitopes of Tumor-Associated Antigens" *PLoS ONE*, 8(12):1-12.
U.S. Appl. No. 10/578,183, filed Feb. 26, 2007, by Sugiyama: Non-Final Office Action, dated Sep. 13, 2017, with Form PTO 1449 (70 pages).
U.S. Appl. No. 13/755,185, filed Jan. 31, 2013, by Sugiyama: Non-Final Office Action, dated Sep. 14, 2017, with Form PTO 1449 (34 pages).
U.S. Appl. No. 13/877,768, filed Jun. 21, 2013, by Sugiyama: Non-Final Office Action, dated Nov. 20, 2017, with Form PTO 1449 (31 pages).
U.S. Appl. No. 13/877,768, file Jun. 21, 2013, by Sugiyama: Final Rejection, dated Dec. 28, 2016, with Form PTO 1449 (21 pages).
Karin et al., Reversal of Experimental Autoimmune Encephalomyelitis by a Soluble Peptide Variant of a Myelin Basic Protein Epitope: T Cell Receptor Antagonism and Reduction of Interferon γ and Tumor.

(56) References Cited

OTHER PUBLICATIONS

Necrosis Factor α Production, J. Exp. Med., 180: 2227-2237 (1994).
Marsh et al., "Nomenclature for factors of HLA system, 2004," Tissue Antigens, 65: 301-369 (2005).
Nikbin et al., "Human Leukocyte Antigen (HLA) Class I and II Polymorphism in Iranian Health Population from Yazd Province," Iran J. Allergy Asthma Immunol, 16(1): 1-13 (2017).
Patel et al., "Identification of immunodominant T cell epitopes of human glutamic acid decarboxylase 65 by using HLA-DR(α1*0101,β1*0401) transgenic mice," Proc. Natl. Acad. Sci. USA, 94: 8082-8087 (1997).
Del Ricon et al., Ethnic Variation in the Clinical Manifestations of Rheumatoid Arthritis: Role of HLA-DRB1 Alleles,: Arthritis & Rheumatism, 49(2): 200-208 (2003).
Rena et al., Clin. Canc. Res. Aug. 2007, 13(15): 4547-5227.
Wang et al., Blood, 2007, 109: 4865-4872.
Office Action dated Sep. 14, 2020, issued in U.S. Appl. No. 15/920,121 (40 pages), Office Action only.
Voskoglou-Nomikos et al.: "Clinical Predictive Value of the in Vitro Cell Line, Human Xenograft, and Mouse Allograft Preclinical Cancer Models", *Clin. Can. Res.* 9: 4227-4239 (2003) (13 pages).
Office Action dated Jan. 17, 2019, issued in U.S. Appl. No. 13/877,768 (14 pages).
"Genetic Testing for Cancer Risk," cancer.net, 2018 (cancer.net/navigating-cancer-care/cancer-basics/genetics/genetic-testing-cancer-risk) (3 pages).
Office Action dated Jan. 17, 2019, issued in U.S. Appl. No. 96/000,259 (10 pages).
Southwood S. et al "Several Common HLA-DR Types Share Largely Overlapping Peptide Binding Repertoires" J Immunol (1998) 160:3363-3373 (12 pages).
Office Action dated May 15, 2019, in U.S. Appl. No. 13/877,768 (10 pages).
Sanmamed, Miguel F. et al., *Agonists of Co-stimulation in Cancer Immunotherapy Directed Against CD137, OX40, GITR, CD27, CD28, and ICOS*, Seminars in Oncology, vol. 42, No. 4, Aug. 2015, pp. 640-655 (16 pages).
Office Action issued in Russian Patent Application No. 2009135802/10(050506).
Issuance of Supplemental Examination in U.S. Appl. No. 96/000,259, dated Oct. 23, 2018 (2 pages).
Reasons for Substantial New Question of Patentability determination in U.S. Appl. No. 96/000,259, dated Oct. 23, 2018 (7 pages).
Ex Parte Reexamination Ordered Pursuant to 35 U.S.C. 257 in U.S. Appl. No. 96/000,259, dated Nov. 16, 2018 (2 pages).
"Do T-cells express MHC molecules?" Biology Stack Exchange, http://biolology.stackexchange.com/questions/5612/do-t-cells-express-mhc-molecules, 2014, 1 page.
International Search Report dated Feb. 8, 2005 in PCT/JP2004/016336, with English language translation, 12 pages.
International Preliminary Report on Patentability dated Sep. 8, 2005 in PCT/JP2004/016336, submitting English translation only, 17 pages.

* cited by examiner

METHOD FOR ACTIVATION OF HELPER T CELL AND COMPOSITION FOR USE IN THE METHOD

CROSS REFERENCE TO RELATED APPLICATIONS

This is a divisional of U.S. application Ser. No. 12/449,765, filed Aug. 26, 2009, which is a § 371(c) national stage application of International Application No. PCT/JP08/053417, filed Feb. 27, 2008, which claims the benefit of priority to Japanese Patent Application No. 2007-047317, filed Feb. 27, 2007, all of which are incorporated herein by reference.

TECHNICAL FIELD

The present invention relates to a method for the activation of a helper T cell, comprising adding a WT1 peptide to an antigen-presenting cell, and thereby activating the helper T cell, wherein the WT1 peptide has an ability to any one of an HLA-DRB1*1501 molecule, HLA-DPB1*0901 molecule and HLA-DPB1*0501 molecule and a composition for the same, a pharmaceutical composition for the treatment and/or prevention of a cancer by activating a helper T cell and the like.

BACKGROUND

WT1 gene (Wilms' tumor 1 gene) was identified as a gene responsible for Wilms tumor which is a renal cancer in children (Non-Patent Documents 1 and 2). WT1 is a transcription factor having a zinc finger structure. At the beginning, the WT1 gene was considered to be a tumor suppressor gene. However, subsequent studies (Non-Patent Documents 3, 4, 5 and 6) showed that the WT1 gene rather functions as an oncogene in hematopoietic tumors and solid cancers.

It was shown that a WT1 peptide-specific T-lymphocyte (CTL) can be induced by in vitro stimulating a peripheral blood mononuclear cell with a WT1 peptide, and such a CTL damages a cancer cell such as a hematopoietic tumor cell and solid cancer cell which endogenously expresses WT1. The CTL recognizes the WT1 peptide as the form of the complex in which the WT1 peptide binds to an MHC class I molecule. Therefore, such a WT1 peptide is different depending on the subtypes of MHC class I (Patent Document 1, Non-Patent Document 7, and Patent Documents 2, 3 and 4).

The existence of a helper T cell specific for an cancer antigen is important to induce a CTL effectively (Non-Patent Document 8). The helper T cell is induced and activated by the recognition of a complex of an MHC class II molecule and an antigen peptide on an antigen-presenting cell. The activated helper T cell produces a cytokine such as IL-2, IL-4, IL-5, IL-6 or interferon to help the growth, differentiation or maturation of a B cell. The activated helper T cell also has a function to facilitate the growth, differentiation or maturation of other T cell subsets (for example, Tc and TD cell). Thus, the activated helper T cell has a function to activate an immune system by facilitating the growth or activation of a B cell or T cell. Therefore, enhancing a function of a helper T cell through an MHC class II-binding antigen peptide (a helper peptide) in a cancer immunotherapy to increase the effect of a cancer vaccine is considered to be useful (Non-Patent Document 9). Only a peptide binding to an HLA-DRB1*0401 molecule (Non-Patent Document 10), a peptide binding to an HLA-DRB1*0405 molecule and a peptide binding to an HLA-DRB1*1502 molecule (Patent Document 5) were found as a helper peptide of WT1 to date. Therefore, there is a need to find peptides each biding to an HLA-DRB1*1501, HLA-DPB1*0901 or HLA-DPB1*0501 molecule.

Furthermore, it was shown that among the helper peptides, there is a promiscuous helper peptide which can bind to multiple MHC class II molecules, and induce helper T cells (Non-Patent Documents 11 and 12). However, it was very difficult to identify a promiscuous helper peptide which binds to three or more types of MHC class II molecules and exerts a sufficient effect.

Patent Document 1: WO 2003/106682
Patent Document 2: WO 2005/095598
Patent Document 3: WO 2007/097358
Patent Document 4: International Patent Application No. PCT/JP2007/074146
Patent Document 5: WO 2005/045027
Non-Patent Document 1: Daniel A. Haber et al., Cell. 1990 Jun. 29; 61(7):1257-69.
Non-Patent Document 2: Call K M et al., Cell. 1990 Feb. 9; 60(3):509-20.
Non-Patent Document 3: Menke A L et al., Int Rev Cytol. 1998; 181:151-212. Review.
Non-Patent Document 4: Yamagami T et al., Blood. 1996 Apr. 1; 87(7):2878-84.
Non-Patent Document 5: Inoue K et al., Blood. 1998 Apr. 15; 91(8):2969-76.
Non-Patent Document 6: Tsuboi A et al., Leuk Res. 1999 May; 23(5):499-505.
Non-Patent Document 7: Oka Y et al., Immunogenetics. 2000 February; 51(2):99-107.
Non-Patent Document 8: Gao F G et al., Cancer Res. 2002 Nov. 15; 62(22):6438-41.
Non-Patent Document 9: Zeng G, J Immunother. 2001 May; 24(3):195-204
Non-Patent Document 10: Knights A J et al., Cancer Immunol Immunother. 2002 July; 51(5):271-81.
Non-Patent Document 11: Sotiriadou R et al., Br J Cancer. 2001 Nov. 16; 85(10):1527-34.
Non-Patent Document 12: Hural J A et al., J Immunol. 2002 Jul. 1; 169(1):557-65.

DISCLOSURE OF INVENTION

Problems to be Solved by the Invention

The problems to be solved by the present invention are to provide to a method for the activation of a helper T cell with a WT1 peptide which has an ability to bind to an HLA-DRB1*1501 molecule, HLA-DPB1*0901 molecule or HLA-DPB1*0501 molecule and a composition for the same, as well as a pharmaceutical composition for the treatment and/or prevention of a cancer by activating a helper T cell and the like.

Means to Solve the Problems

As a result of intensive studies in view of the situation as described above, the present inventor has found that among WT1 peptides which bind to an HLA-DRB1*0405 molecule and HLA-DRB1*1502 molecule, a WT1 peptide having an amino acid sequence: Lys Arg Tyr Phe Lys Leu Ser His Leu Gln Met His Ser Arg Lys His (SEQ ID NO: 2) also binds to an HLA-DRB1*1501 molecule, HLA-DPB1*0901 molecule and HLA-DPB1*0501 molecule. Thus, the present invention has been completed.

The present invention provides:

(1) a method for the activation of a helper T cell, comprising adding a Wt 1 peptide to an antigen-presenting cell, and thereby activating the helper T cell, wherein the WT1 peptide has an ability to bind to any one of an HLA-DRB1*1501 molecule, HLA-DPB1*0901 molecule and HLA-DPB1*0501 molecule;

(2) the method according to (1), wherein the WT1 peptide has an ability to bind to at least two of an HLA-DRB1*1501 molecule, HLA-DPB1*0901 molecule and HLA-DPB1*0501 molecule;

(3) the method according to (1) or (2), wherein the WT1 peptide further has an ability to bind to an HLA-DRB1*0405 molecule and/or HLA-DRB1*1502 molecule;

(4) the method according to any one of (1)-(3), wherein the WT1 peptide has an ability to bind to an HLA-DRB1*1501 molecule, HLA-DPB1*0901 molecule, HLA-DPB1*0501 molecule, HLA-DRB1*0405 molecule and HLA-DRB1*1502 molecule;

(5) the method according to any one of (1)-(4), wherein the WT1 peptide is a peptide comprising an amino acid sequence: Lys Arg Tyr Phe Lys Leu Ser His Leu Gln Net His Ser Arg Lys His (SEQ ID No: 2);

(6) the method according to any one of (1)-(5), wherein the addition of the WT1 peptide to the antigen-presenting cell is practiced by the addition of the WT1 peptide, the addition of n expression vector comprising the polynucleotide encoding the WT1 peptide or the addition of a cell including the expression vector;

(7) a composition for activating a helper T cell by the addition of a WT1 peptide to an antigen-presenting cell, comprising the WT1 peptide, wherein the WT1 peptide has an ability to bind to any one of an HLA-DRB1*1501 molecule, HLA-DPB1*0901 molecule and HLA-DPB1*0501 molecule;

(8) a method for the treatment or prevention of a cancer in a subject, comprising adding a WT1 peptide to an antigen-presenting cell, and thereby activating a helper T cell, wherein the WT1 peptide has an ability to bind to any one of an HLA-DRB1*1501 molecule, HLA-DPB1*0901 molecule and HLA-DPB1*0501 molecule;

(9) a pharmaceutical composition for the treatment or prevention of a cancer by activating a helper T cell by the addition of a WT1 peptide to an antigen-presenting cell, comprising the WT1 peptide, wherein the WT1 peptide has an ability to bind to any one of an HLA-DRB1*1501 molecule, HLA-DPB1*0901 molecule and HLA-DPB1*0501 molecule;

(10) an antibody binding specifically to a WT1 peptide, wherein the WT1 peptide has an ability to bind to any one of an HLA-DRB1*1501 molecule, HLA-DPB1*0901 molecule and HLA-DPB1*0501 molecule;

(11) a method for the determination of the presence or amount of a WT1 peptide in any one of an HLA-DRB1*1501-positive, HLA-DPB1*0901-positive and HLA-DPB1*0501-positive subject, comprising:

(a) reacting an anti-WT1 antibody with a sample from the subject; and (b) determining the presence or amount of the anti-WT1 antibody binding specifically to the WT1 peptide contained in the sample;

(12) a method for the treatment or prevention of a cancer, comprising adding a WT1 peptide to an antigen-presenting cell, and thereby activating a helper T cell, and administering the activated helper T cell to a subject, wherein the WT1 peptide has an ability to bind to an HLA-DRB1*1501 molecule, HLA-DPB1*0901 molecule or HLA-DPB1*0501 molecule;

(13) a pharmaceutical composition for the treatment or prevention of a cancer, comprising a helper T cell activated with a WT1 peptide, wherein the WT1 peptide has an ability to bind to any one of an HLA-DRB1*1501 molecule, HLA-DPB1*0901 molecule and HLA-DPB1*0501 molecule;

(14) a method for the determination of the presence or amount of a WT1-specific helper T cell in any one of an HLA-DRB1*1501-positive, HLA-DPB1*0901-positive and HLA-DPB1*0501-positive subject, comprising:

(a) reacting a complex of a WT1 peptide and an HLA-DRB1*1501 molecule, HLA-DPB1*0901 molecule or HLA-DPB1*0501 molecule with a sample from the subject; and (b) determining the presence or amount of a helper T cell recognizing the complex contained in the sample; and

(15) a method for the determination of the presence or amount of a WT1-specific helper T cell in an HLA-DRB1*1501-positive, HLA-DPB1*0901-positive, HLA-DPB1*0501-positive, HLA-DRB1*0405-positive or HLA-DRB1*1502-positive subject, comprising:

(a) stimulating a peripheral blood mononuclear cell, invasive lymphocyte, tumor cell, cell in ascitic fluid, cell in pleural fluid, cell in cerebrospinal fluid, bone marrow cell or lymph node cell with a WT1 peptide; and (b) determining the production of a cytokine or the reaction of the helper T cell, wherein a presence or an increase in the amount of the production of the cytokine or the reaction of the helper T cell indicates the presence or amount of the WT1-specific helper T cell.

Effects of the Invention

The present invention provides a method for the activation of a helper T cell with a WT1 peptide which binds to an HLA-DRB1*1501 molecule, HLA-DPB1*0901 molecule, HLA-DPB1*0501 molecule, HLA-DRB1*0405 molecule, and HLA-DRB1*1502 molecule and a composition for the same, as well as a pharmaceutical composition for the treatment and/or prevention of a cancer by activating a helper T cell, and the like. Therefore, it is possible to activate in vivo and in vitro a helper T cell in the subject having any of such MHC class II molecules, treat and prevent a cancer and the like. Because about 90% of Japanese people are covered by the five types of MHC class II subclasses, helper T cells can be activated to treat and/or prevent a cancer in a very wide range of subjects.

BRIEF DESCRIPTION OF DRAWINGS

FIG. 4 a represents the cells without stimulating with the WT1 peptide, and FIG. 4 b represents the cells stimulated with the WT1 peptide.

BEST MODE FOR CARRYING OUT THE INVENTION

Figure 1:
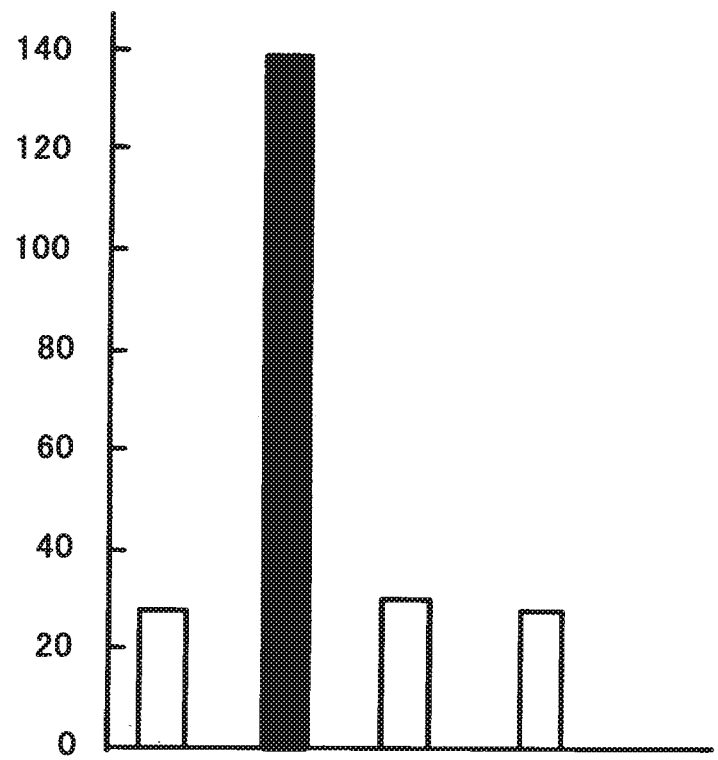
FIG. 1 is a graph which represents the amount of IFN-γ produced by TA28.1 cell. In the figure, a longitudinal axe represents concentration of IFN-γ (pg/ml). The graphs correspond to "the case of culturing peripheral blood mononuclear cells from an HLA-DRB1*1501-positive subject in the absence of the WT1 peptide", "the case of culturing TA28.1 cells in the presence of the WT1 peptide (black)", "the case of culturing peripheral blood mononuclear cells from an HLA-DRB1*1501-negative subject in the absence of the WT1 peptide", "the case of culturing peripheral blood mononuclear cells from an HLA-DRB1*1501-negative subject in the presence of the WT1 peptide" starting from the left, respectively.

In one aspect, the present invention relates to a method for the activation of a helper T cell, comprising adding a WT1 peptide to an antigen-presenting cell, and thereby activating the helper T cell, wherein the WT1 peptide has an ability to bind to any one of an HLA-DRB1*1501 molecule, HLA-DPB1*0901 molecule and HLA-DPB1*0501 molecule. In the present invention, the WT1 peptide refers a peptide consisting of a part of the amino acid sequence of human WT1 protein shown in SEQ ID No: 1, a peptide which has a substitution, modification, or deletion of one to several amino acids in the amino acid sequence, and has an ability to bind to any one of an HLA-DRB1*1501 molecule, HLA-DPB1*0901 molecule and HLA-DPB1*0501 molecule, or a peptide in which various substances such as an amino acid, a peptide or an analog thereof may be attached at the N-terminus and/or the C-terminus of the peptide. The substance can be processed, for example, by an enzyme in a living body or through a process such as intracellular processing, and finally the WT1 peptide becomes the form which can bind to any one of an HLA-DRB1*1501 molecule, HLA-DPB1*0901 molecule and HLA-DPB1*0501 molecule. The substance may be a substance that modulates the solubility of the WT1 peptide of the present invention, or increases its stability (resistance to protease, etc.). Alternatively, it may be a substance that delivers the WT1 peptide of the present invention specifically, for example, to a given tissue or organ, or increases the efficiency of uptake by an antigen-presenting cell or the like. Alternatively, it may be a WT1 peptide which is restricted to the same type of an MHC class I molecule as that of a subject from which an antigen-presenting cell is derived.

The WT1 peptide of the present invention has an ability to bind to any one of an HLA-DRB1*1501 molecule, HLA-DPB1*0901 molecule and HLA-DPB1*0501 molecule. Thus, the WT1 peptide may be a peptide which has an ability to bind to at least two of an HLA-DRB1*1501 molecule, HLA-DPB1*0901 molecule and HLA-DPB1*0501 molecule, or a peptide that has an ability to bind to an HLA-DRB1*1501 molecule and/or HLA-DPB1*0901 molecule and/or HLA-DPB1*0501 molecule, and an HLA class II molecule other than the molecules, for example, a peptide which has an ability to bind to an HLA-DRB1*1501 molecule, HLA-DRB1*0405 molecule and/or HLA-DRB1*1502 molecule, a peptide which has an ability to bind to an HLA-DPB1*0901 molecule, HLA-DRB1*0405 molecule and/or HLA-DRB1*1502 molecule, a peptide which has an ability to bind to an HLA-DPB1*0501 molecule, HLA-DRB1*0405 molecule and/or HLA-DRB1*1502 molecule, or a peptide which has an ability to bind to an HLA-DRB1*1501 molecule, HLA-DPB1*0901 molecule, HLA-DPB1*0501 molecule, HLA-DRB1*0405 molecule and/or HLA-DRB1*1502 molecule. Because a WT1 peptide having an amino acid sequence: Lys Arg Tyr Phe Lys Leu Ser His Leu Gln Met His Ser Arg Lys His (SEQ ID No: 2) has an ability to bind to an HLA-DRB1*1501 molecule, an HLA-DPB1*0901 molecule, an HLA-DPB1*0501 molecule, an HLA-DRB1*0405 molecule and an HLA-DRB1*1502 molecule, the WT1 peptide having such an amino acid sequence is preferable. In general, an MHC class II-binding peptide consists of 10-25 amino acids. Therefore, the WT1 peptide preferably has an amino acid sequence consisting of 10-25 amino acids.

The WT1 peptide of the present invention can be synthesized by methods generally used in the art or modifications thereof. Such methods are described, for example, in Peptide Synthesis, Interscience, New York, 1966; The Proteins, Vol 2, Academic Press Inc., New York, 1976; Peptide-Gosei, Maruzen Co., Ltd., 1975; Peptide-Gosei No Kiso To Jikken, Maruzen Co., Ltd., 1985; and Iyakuhin No Kaihatsu (Zoku), Vol. 14, Peptide-Gosei, Hirokawa—Book store, 1991.

The WT1 peptide of the present invention can also be prepared using genetic engineering techniques based on the information about the nucleotide sequence that encodes the WT1 peptide. Such genetic engineering techniques are well known to a person skilled in the art.

The antigen-presenting cell refers to a cell such as a dendritic cell which can present the WT1 peptide together with a MHC class II molecule to a helper T cell or the like. Thus, a subject from which the antigen-presenting cell is derived must have the same subclass of MHC class II (for example, HLA-DRB1*1501, HLA-DPB1*0901, HLA-DPB1*0501, HLA-DRB1*0405 or HLA-DRB1*1502) as that to which the added WT1 peptide binds.

In general, a helper T cell is activated by the recognition of an antigen peptide through an MHC class II molecule on the surface of an antigen-presenting cell by TCR-CD3 complex on the surface of the T cell, and the stimulation of an integrin on the surface of the T cell by an integrin ligand on the surface of the antigen-presenting cell. In the present invention, the activation of the helper T cell encompasses not only the activation of the helper T cell but also the induction and growth of the helper T cell. As described above, the activated helper T cell has a function to activate an immune system by increasing the induction, growth or activation of a B cell or T cell. Thus, the method for the activation of a helper T cell of the present invention can be used as an adjuvant therapy in the treatment of a cancer or the like. Alternatively, the helper T cell activated in vitro using the method of the present invention can be used to treat or prevent a cancer or the like, or can be used as an adjuvant therapy in the same. The activation of the helper T cell can be determined by measuring the amount of the production or secretion of a cytokine such as an interferon and an interleukin, and the like.

The addition of the WT1 peptide to the antigen-presenting cell may be practiced directly by the addition of the WT1 peptide, or indirectly by the addition of an expression vector comprising a polynucleotide encoding the WT1 peptide or the addition of a cell comprising the expression vector. The expression vector comprising the polynucleotide encoding the WT1 peptide, and the cell comprising the expression vector can be produced by the method well known to the person skilled in the art.

In another aspect, the present invention relates to a composition for activating a helper T cell by the addition of a WT1 peptide to an antigen-presenting cell, comprising the WT1 peptide, wherein the WT1 peptide has an ability to bind to any one of an HLA-DRB1*1501 molecule, HLA-DPB1*0901 molecule and HLA-DPB1*0501 molecule. When the composition of the present invention is administered to an HLA-DRB1*1501, HLA-DPB1*0901 or HLA-DPB1*0501-positive subject, an immune system in the subject is activated by the activation of the helper T cell in the subject. The WT1 gene is expressed at high levels in various cancers and tumors including hematopoietic tumors such as leukemia, myelodysplastic syndrome, multiple myeloma or malignant lymphoma, and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer. Therefore, the composition of the present invention can be used as an adjuvant therapy in the treatment or prevention of a cancer. Alternatively, the helper T cell activated using the composition of the present invention can be used, for example, as an adjuvant in the treatment of a cancer.

As described above, the WT1 peptide of the present invention may be a peptide which has an ability to bind to at least two of an HLA-DRB1*1501 molecule, HLA-DPB1*0901 molecule and HLA-DPB1*0501 molecule, or a peptide which has an ability to bind to an HLA-DRB1*1501 molecule and/or HLA-DPB1*0901 molecule and/or HLA-DPB1*0501 molecule, and an MHC class II molecule other than them. Thus, as long as the antigen-presenting cell is derived from a subject positive for an MHC class II subclass to which the WT1 peptide of the present invention can bind, the effect of activating the helper T cell of the composition of the present invention can result.

The composition of the present invention may comprise in addition to the WT1 peptide, for example, a carrier, an excipient, an additive or the like. Because the WT1 peptide comprised in the composition of the present invention activate the helper peptide specifically to the WT1 peptide, the composition may comprise an MHC class I-restricted WT1 peptide, or it may be used with the peptide.

The method for using the composition of the present invention can be appropriately selected depending on conditions such as the desired activation of the helper T cell, the state of the antigen-presenting cell. Examples of such methods include, but are not limited to, intradermal administration, subcutaneous administration, intramuscular administration, intravenous administration, nasal administration and oral administration, and the addition to a culture medium of the antigen-presenting cell. The amount of the WT1 peptide comprised in the composition of the present invention, as well as the form, the number of times of use the like of the composition of the present invention can be appropriately selected depending on conditions such as the desired activation of the helper T cell, the state of the antigen-presenting cell.

In a further aspect, the present invention relates to a composition for activating a helper T cell by the addition of a WT1 peptide to an antigen-presenting cell, comprising an expression vector comprising a polynucleotide encoding the WT1 peptide or a cell comprising the expression vector, wherein the WT1 peptide has an ability to bind to any one of an HLA-DRB1*1501 molecule, HLA-DPB1*0901 molecule and HLA-DPB1*0501 molecule. The expression vector comprising the polynucleotide encoding the WT1 peptide and the cell comprising the expression vector are described above.

In another aspect, the present invention relate to use of an expression vector comprising a polynucleotide encoding a WT1 peptide, or a cell comprising the expression vector for the manufacture of the composition.

In a further aspect, the present invention relates to a kit for activating a helper T cell by the addition of a WT1 peptide to an antigen-presenting cell, comprising the WT1 peptide, wherein the WT1 peptide has an ability to bind to any one of an HLA-DRB1*1501 molecule, HLA-DPB1*0901 molecule and HLA-DPB1*0501 molecule. Preferably, the kit is used in the method for the activation of a helper T cell. The kit of the present invention may comprise in addition to the WT1 peptide, for example, a means of obtaining an antigen-presenting cell, a means to determine a helper T cell activity or the like. In general, an instruction manual is attached to the kit. By using the kit of the present invention, helper T cells can be induced efficiently.

In another aspect, the present invention relates to a kit for activating a helper T cell by the addition of a WT1 peptide to an antigen-presenting cell, comprising an expression vector comprising a polynucleotide encoding WT1 peptide, or a cell comprising the expression vector, wherein the WT1 peptide has an ability to bind to any one of an HLA-DRB1*1501 molecule, HLA-DPB1*0901 molecule and HLA-DPB1*0501 molecule.

In another aspect, the present invention relates to a method for the treatment or prevention of a cancer in a subject, comprising adding a WT1 peptide to an antigen-presenting cell, and thereby activating a helper T cell, wherein the WT1 peptide has an ability to bind to any one of an HLA-DRB1*1501 molecule, HLA-DPB1*0901 molecule and HLA-DPB1*0501 molecule. The method of the present invention is a method in which an immune system in the subject is activated by the activation of a helper T cell, and a cancer in the subject is treated or prevented. The addition of the WT1 peptide to the antigen-presenting cell may be practiced directly by the addition of the WT1 peptide, or indirectly by the addition of an expression vector comprising a polynucleotide encoding the WT1 peptide or the addition of a cell comprising the expression vector.

As described above, the helper T cell recognizes the complex of any one of MHC class II molecules, particularly an HLA-DRB1*1501 molecule, HLA-DPB1*0901 molecule or HLA-DPB1*0501 molecule and the WT1 peptide. Therefore, the subject is a subject having an MHC class II molecule to which the WT1 peptide binds, for example, HLA-DRB1*1501-positive, HLA-DPB1*0901-positive or HLA-DPB1*0501-positive subject. As described above, the WT1 peptide of the present invention may be a peptide which has an ability to bind to at least two of an HLA-DRB1*1501 molecule, HLA-DPB1*0901 molecule and HLA-DPB1*0501 molecule, or a peptide which has an ability to bind to an HLA-DRB1*1501 molecule and/or HLA-DPB1*0901 molecule and/or HLA-DPB1*0501 molecule, and an MHC class II molecule other than them. Thus, in such a case, it is possible to treat or prevent a cancer in a subject positive for an MHC class II subclass to which the WT1 peptide of the present invention can bind. The cancer to be treated or prevented may be any one, and examples thereof include hematopoietic tumors such as leukemia, myelodysplastic syndrome, multiple myeloma or malignant lymphoma, and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer. Furthermore, the method of the present invention may be used with a method for the treatment or prevention of a cancer with an MHC class I molecule-restricted WT1 peptide or a pharmaceutical composition for the same.

In another aspect, the present invention relates to a pharmaceutical composition for the treatment or prevention of a cancer in a subject by activating a helper T cell by the addition of a WT1 peptide to an antigen-presenting cell, comprising the WT1 peptide, wherein the WT1 peptide has an ability to bind to any one of an HLA-DRB1*1501 molecule, HLA-DPB1*0901 molecule and HLA-DPB1*0501 molecule. The WT1 gene is expressed at high levels in various cancers and tumors including hematopoietic tumors such as leukemia, myelodysplastic syndrome, multiple myeloma or malignant lymphoma, and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer. Therefore, the pharmaceutical composition of the present invention can be used for the treatment or prevention of a cancer.

As described above, the WT1 peptide of the present invention may be a peptide which has an ability to bind to at least two of an HLA-DRB1*1501 molecule, HLA-DPB1*0901 molecule and HLA-DPB1*0501 molecule, or a peptide which has an ability to bind to an HLA-DRB1*1501 molecule and/or HLA-DPB1*0901 molecule and/or HLA-DPB1*0501 molecule, and an MHC class II molecule other than them. Thus, as long as the antigen-presenting cell is derived from a subject positive for an MHC class II subclass to which the WT1 peptide of the present invention can bind, the pharmaceutical composition of the present invention can be used to treat or prevent a cancer.

When the pharmaceutical composition of the present invention is administered to, for example, an HLA-DRB1*1501-positive, HLA-DPB1*0901-positive or HLA-DPB1*0501-positive subject, an immune system in a subject can be activated by the activation of the helper T cell by the WT1 peptide comprised in the pharmaceutical composition, thereby treating or preventing a cancer. Thus, the pharmaceutical composition of the present invention may be used together with the method for the treatment or prevention of a cancer or the pharmaceutical composition for the same.

The pharmaceutical composition of the present invention may comprise in addition to the WT1 peptide as an active ingredient, for example, a carrier, an excipient or the like. The WT1 peptide comprised in the pharmaceutical composition of the present invention binds to an MHC class II molecule on the surface of an antigen-presenting cell and activates a helper T cell. Therefore, the pharmaceutical composition of the present invention may further comprise an activator, growth factor, inducer or the like of the helper T cell, or may comprise an MHC class I-restricted WT1 peptide.

The method for administering the pharmaceutical composition of the present invention can be appropriately selected depending on conditions such as the type of disease, the condition of the subject or target site. Examples of such methods include, but are not limited to, intradermal administration, subcutaneous administration, intramuscular administration, intravenous administration, nasal administration and oral administration. The amount of the peptide comprised in the pharmaceutical composition of the present invention, as well as the dosage form, the number of times of the administration and the like of the pharmaceutical composition of the present invention can be appropriately selected depending on conditions such as the type of disease, the condition of the subject or the target site. The single dose of the peptide is usually, 0.0001 mg-1000 mg, preferably, 0.001 mg-1000 mg.

In a further aspect, the present invention relates to a pharmaceutical composition for the treatment or prevention of a cancer in a subject by activating a helper T cell by the addition of a WT1 peptide to an antigen-presenting cell, comprising an expression vector comprising a polynucleotide encoding the WT1 peptide, or a cell comprising the expression vector, wherein the WT1 peptide has an ability to bind to any one of an HLA-DRB1*1501 molecule, HLA-DPB1*0901 molecule and HLA-DPB1*0501 molecule.

In a further aspect, the present invention relates to use of a WT1 peptide, an expression vector comprising a polynucleotide encoding the WT1 peptide, or a cell comprising the expression vector for the manufacture of the pharmaceutical composition.

In another aspect, the present invention relates to an antibody binding specifically to a WT1 peptide, wherein the WT1 peptide has an ability to bind to any one of an HLA-DRB1*1501 molecule, an HLA-DPB1*0901 molecule and HLA-DPB1*0501 molecule. The antibody of the present invention can be prepared by the means or method known to the person skilled in the art. The antibody of the present invention can be used for the diagnosis of various cancers, prognosis thereof or the like.

In another aspect, the present invention relates to a method for the determination of the presence or amount of a WT1 peptide in an HLA-DRB1*1501-positive, HLA-DPB1*0901-positive or HLA-DPB1*0501-positive subject, comprising:

(a) reacting an anti-WT1 antibody with a sample form the subject; and (b) determining the presence or amount of the anti-WT1 antibody binding specifically to the WT1 peptide contained in the sample. For example, it is possible to diagnose a cancer, prognosis thereof or the like by incubating the anti-WT1 antibody with a sample from an HLA-DRB1*1501-positive, HLA-DPB1*0901-positive or HLA-DPB1*0501-positive subject, or administering the anti-WT1 antibody to an HLA-DRB1*1501-positive, HLA-DPB1*0901-positive or HLA-DPB1*0501-positive subject, and determining, for example, the position, site or amount thereof. The anti-WT1 antibody of the present invention refers to an antibody which can specifically recognize the WT1 peptide of the present invention. The anti-WT1 antibody may be a monoclonal antibody or polyclonal antibody. The anti-WT1 antibody may be labeled. A known label such as a fluorescent label or a radioactive label can be used as a label. By labeling it, the presence or amount of the WT1 peptide can be determined readily and rapidly.

In another aspect, the present invention relates to a kit for the determination of the presence or amount of a WT1 peptide comprising the anti-WT1 antibody as an essential component.

Furthermore, in the determination of the presence or amount of the WT1 peptide, when the WT1 peptide has an ability to bind to an HLA-DRB1*0405 molecule and/or HLA-DRB1*1502 molecule, it is possible to determine the presence or amount of the WT1 peptide in a subject with such an MHC class II subclass.

In another aspect, the present invention relates to a pharmaceutical composition for the treatment or prevention of a cancer, comprising a helper T cell activated with a WT1 peptide, wherein the WT1 peptide has an ability to bind to an any one of an HLA-DRB1*1501 molecule, HLA-DPB1*0901 molecule and HLA-DPB1*0501 molecule. The cancer is treated or prevented by the induction, growth or activation of a B cell or T cell by the activated helper T cell. Thus, the pharmaceutical composition of the present invention in this aspect may be used together with another method for the treatment or prevention of a cancer or pharmaceutical composition for the same. The activation of the helper T cell with the WT1 peptide encompasses not only the direct activation with the WT1 peptide but also indirect activation with an expression vector comprising a polynucleotide encoding the WT1 peptide or a cell comprising the expression vector.

The pharmaceutical composition of the present invention may comprise in addition to the activated helper T cell as an active ingredient, for example, a carrier, an excipient or the like. The method for administering the pharmaceutical composition of the present invention can be appropriately selected depending on conditions such as the type of disease, the condition of the subject or the target site. Examples of such methods include, but are not limited to, intradermal administration, subcutaneous administration, intramuscular administration, intravenous administration, nasal administration and oral administration. The amount of the helper T cell comprised in the pharmaceutical composition of the present invention, as well as the dosage form, the number of times of the administration and the like of the pharmaceutical composition of the present invention can be appropriately selected depending on a condition such as the type of disease, the condition of the subject or the target site.

In another aspect, the present invention relates to a method for the treatment or prevention of a cancer, comprising adding a WT1 peptide to an antigen-presenting cell, and thereby activating a helper T cell, and administering the activated helper T cell to a subject, wherein the WT1 peptide has an ability to bind to any one of an HLA-DRB1*1501 molecule, HLA-DPB1*0901 molecule and HLA-DPB1*0501 molecule.

In another aspect, the present invention relates to use of a WT1 peptide for the manufacture of the pharmaceutical composition comprising an activated helper T cell.

In a further aspect, the present invention relates to a method for the determining the presence or amount of a WT1-specific helper T cell in any one of an HLA-DRB1*1501-positive, HLA-DPB1*0901-positive and HLA-DPB1*0501-positive subject, comprising:

(a) reacting a complex of a WT1 peptide and an HLA-DRB1*1501 molecule, HLA-DPB1*0901 molecule or HLA-DPB1*0501 molecule with a sample from the subject; and (b) determining the presence or amount of a helper T cell recognizing the complex contained in the sample. The sample from the subject may be any one as long as there is a possibility that it contains a lymphocyte. Examples of the samples include body fluid such as blood or lymph and a tissue. The complex of a WT1 peptide and an HLA-DRB1*1501 molecule, HLA-DPB1*0901 molecule or HLA-DPB1*0501 molecule may be prepared, for example, as a tetramer or pentamer using a method known to a person skilled in the art such as biotin-streptavidin method. The presence or amount of the helper T cell recognizing such a complex can be measured by a method known to a person skilled in the art. In this aspect of the present invention, the complex may be labeled. A known label such as a fluorescent label or a radioactive label can be used as a label. By labeling it, the presence or amount of the helper T cell can be rapidly or readily determined. The method of the present invention in this aspect can be used to diagnose a cancer, prognosis thereof or the like.

Thus, the present invention also provides composition for the determination of the presence or amount of a helper T cell in any one of an HLA-DRB1*1501-positive, HLA-DPB1*0901-positive and HLA-DPB1*0501-positive subject, comprising a complex of a WT1 peptide and an HLA-DRB1*1501 molecule, HLA-DPB1*0901 molecule or HLA-DPB1*0501 molecule.

Furthermore, the present invention provides a kit for the determination of the presence or amount of a helper T cell in an HLA-DRB1*1501-positive, HLA-DPB1*0901-positive or HLA-DPB1*0501-positive subject, comprising a complex of a WT1 peptide and an HLA-DRB1*1501 molecule, HLA-DPB1*0901 molecule or HLA-DPB1*0501 molecule.

Furthermore, in the determination of the presence or amount of the helper T cell, when the WT1 peptide has an ability to an HLA-DRB1*0405 molecule and/or HLA-DRB1*1502 molecule in the determination of the presence or amount of the helper T cell, it is possible to determine the presence or amount of the helper T cell in a subject with such an MHC class II subclass. In such a case, a complex of a WT1 peptide and a MHC class II molecule to which the WT1 peptide binds is used.

In a further aspect, the present invention relates to a method for the obtainment of a helper T cell using a complex of a WT1 peptide and an HLA-DRB1*1501 molecule, HLA-DPB1*0901 molecule or HLA-DPB1*0501 molecule, comprising:

(a) reacting a sample with the complex; and (b) obtaining a helper T cell recognizing the complex contained in the sample. The complex is described above. The sample may be any one as long as there is a possibility that it contains a lymphocyte. Examples of the samples include a sample from a subject such as blood, and a cell culture. The helper T cell recognizing the complex can be obtained using a method known to a person skilled in the art such as FACS or MACS. The present invention allows to culture the obtained helper T cell and use it for the treatment or prevention of various cancers.

Thus, the present invention also relates to a helper T cell which is obtainable by a method for obtaining a helper T cell using a complex of a WT1 peptide and an HLA-DRB1*1501 molecule, HLA-DPB1*0901: molecule or HLA-DPB1*0501 molecule.

Furthermore, the present invention relates to a kit for obtaining a helper T cell, comprising a complex of a WT1 peptide and an HLA-DRB1*1501 molecule, HLA-DPB1*0901 molecule or HLA-DPB1*0501 molecule.

Furthermore, in obtaining the helper T cell, when the WT1 peptide has an ability to bind to an HLA-DRB1*0405 molecule and/or HLA-DRB1*1502 molecule, it is possible to obtain a helper T cell recognizing a complex of such an MHC class II subclass and a WT1 peptide. In such a case, the complex of the WT1 peptide and an MHC class II molecule to which it binds is used.

In another aspect, the present invention relates to a method for the determination of the presence or amount of a WT1-specific helper T cell in an HLA-DRB1*1501-positive, HLA-DPB1*0901-positive, HLA-DPB1*0501-positive, HLA-DRB1*0405-positive or HLA-DRB1*1502-positive subject, comprising:

(a) stimulating a peripheral blood mononuclear cell, invasive lymphocyte, tumor cell, cell in ascitic fluid, cell in pleural fluid, cell in cerebrospinal fluid, bone marrow cell or lymph node cell with a WT1 peptide; and (b) determining the production of a cytokine or the reaction of the helper T cell, wherein a presence or an increase in the amount of the production of the cytokine or the reaction of the helper T cell indicates the presence or amount of the WT1-specific helper T cell. The cells such as the peripheral blood mononuclear cell, invasive lymphocyte, tumor cell, cell in ascitic fluid, cell in pleural fluid, cell in cerebrospinal fluid, bone marrow cell and lymph node cell used in the method of the present invention may be derived from a healthy subject or a cancer patient. By using the cells from a healthy subject, it is possible to determine whether or not the subject is suffering from a cancer, whether or not the subject has the predisposition thereof or the like. By using the cells from a cancer patient, it is possible to predict whether or not WT1-immunnotherapy has a effect on the cancer patient or the like. The stimulation of the cells with the WT1 peptide may be practiced in vitro or in vivo. Because of easiness, in vitro stimulation is preferable. The presence of the production of the cytokine or the reaction of the helper T cell, or the amount of the production of the cytokine or the reaction of the helper T cell can be determined by a known method.

The following examples illustrate the present invention in more detail, but are not to be construed to limit the scope thereof.

Examples

1. Preparation of Antigen-Presenting Cell

Peripheral blood mononuclear cells (PBMCs) were separated from peripheral blood that had been collected from a healthy donor (HLA-DRB1*1501-positive, HLA-DPB1*0901-positive or HLA-DPB1*0501-positive). The PBMCs were seeded to a 6-well plastic plate at the density of 1×107 cells/well in 1% AB serum (Nabi, Miami, Fla.), X-VIVO 15 medium (Cambrex), and cultured for 2 hours. After the culture, suspension cells were removed, and the remaining adherent cells were cultured in 1000 IU/ml IL-4 (PeproTech), 1000 IU/ml GM-CSF (PeproTech), 1% AB serum and X-VIVO 15 medium. On day 2 and day 4, the medium was changed, and IL-4 and GM-CSF were added. On day 6, 100 IU/ml TNF-α was added to mature antigen-presenting cells.

2. Induction of WT1 Peptide-Specific CD4-Positive T Cell

CD4-positive T cells were separated from blood derived from the same donor using RosetteSep for the separation of CD4-positive T cells (StemCell). The CD4-positive T cells (3×106 cells) were added to each well of a 24-well plate. They were stimulated with autologous antigen-presenting cells (3×105 cells) that had been pulsed with 20 μg/ml WT1 peptide (SEQ ID No: 2), and irradiated with 25 Gy of radiation. On next day after the stimulation, 20 IU/ml IL-2 was added. Likewise, the stimulated CD4-positive T cells were stimulated using the antigen-presenting cells pulsed with 20 μg/ml WT1 peptide every other week. Furthermore, the medium was changed to the medium containing IL-2 every other day after second stimulation. The CD4-positive T cells induced by total three times of stimulation (HLA-DRB1*1501 and HLA-DPB1*0901-positive T cells were defined as TA28.1 cell and E15.2 cell, respectively) were used for experiments below.

3. Measurement of IFN-γ

TA28.1 cells and peripheral blood mononuclear cells from a subject from which the TA28.1 cells were derived were cultured in the presence of 20 μg/ml WT1 peptide for 24 hours. After the culture, the amount of IFN-γ in the supernatant was quantified using ELISA kit. As a control, a peripheral blood mononuclear cell from an HLA-DRB1*1501-negative subject was used. The results are shown in FIG. 1. It was confirmed that TA28.1 cell recognizes the WT1 peptide specifically to an HLA-DRB1*1501 molecule to increase the produced amount of IFN-γ (that is, activation).

Figure 2:
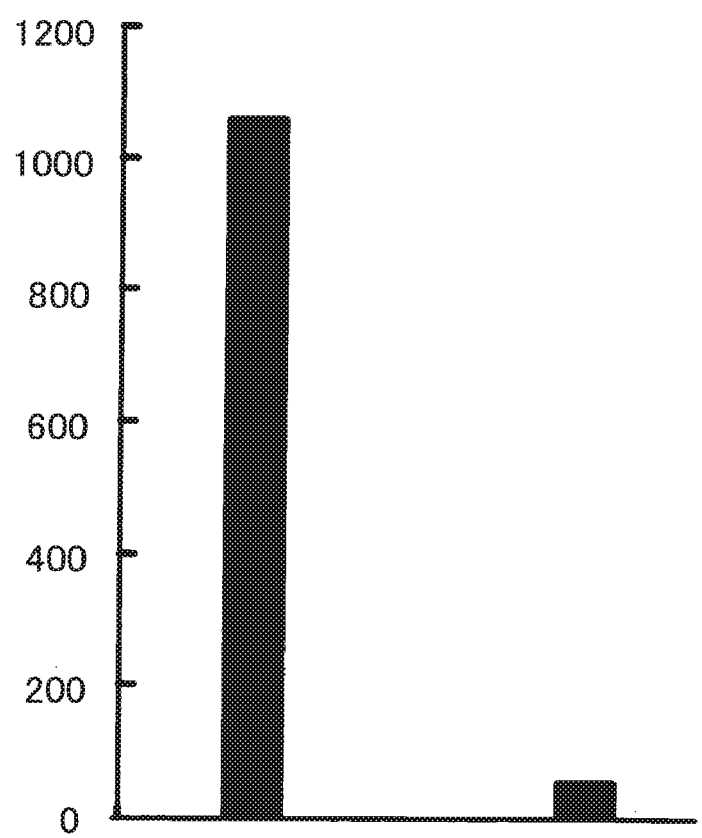
FIG. 2 is a graph which represents the amounts of IFN-γ, IL-4 and IL-10 produced by TA28.1 cell. In the figure, a longitudinal axe represents concentration (pg/ml). The graphs correspond the values of IFN-γ, IL-4 and IL-10 starting from the left.
Figure 3:
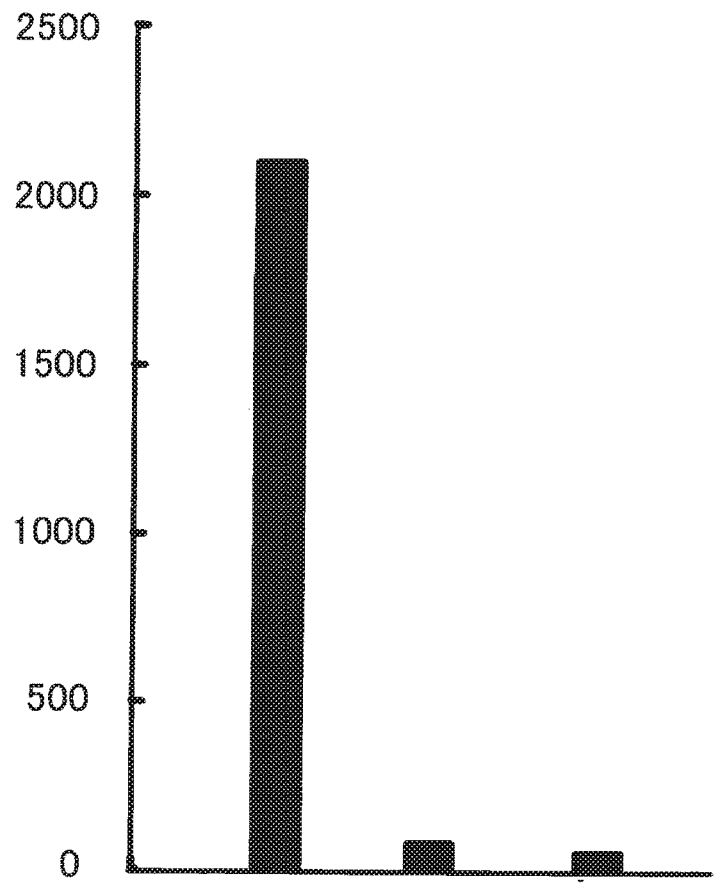
FIG. 3 is a graph which represents the amounts of IFN-γ, IL-4 and IL-10 produced by E15.2 cell. In the figure, a longitudinal axe represents concentration (pg/ml). The graphs correspond to the values of IFN-γ, IL-4 and IL-10 starting from the left.

Furthermore, it was confirmed that TA28.1 cell and E15.2 cell do not produce IL-4 and IL-10 using ELISA kit. The results are shown in FIGS. 2 and 3. It was confirmed that TA28.1 and E15.2 cell are Th1 cells.

Figure 4:
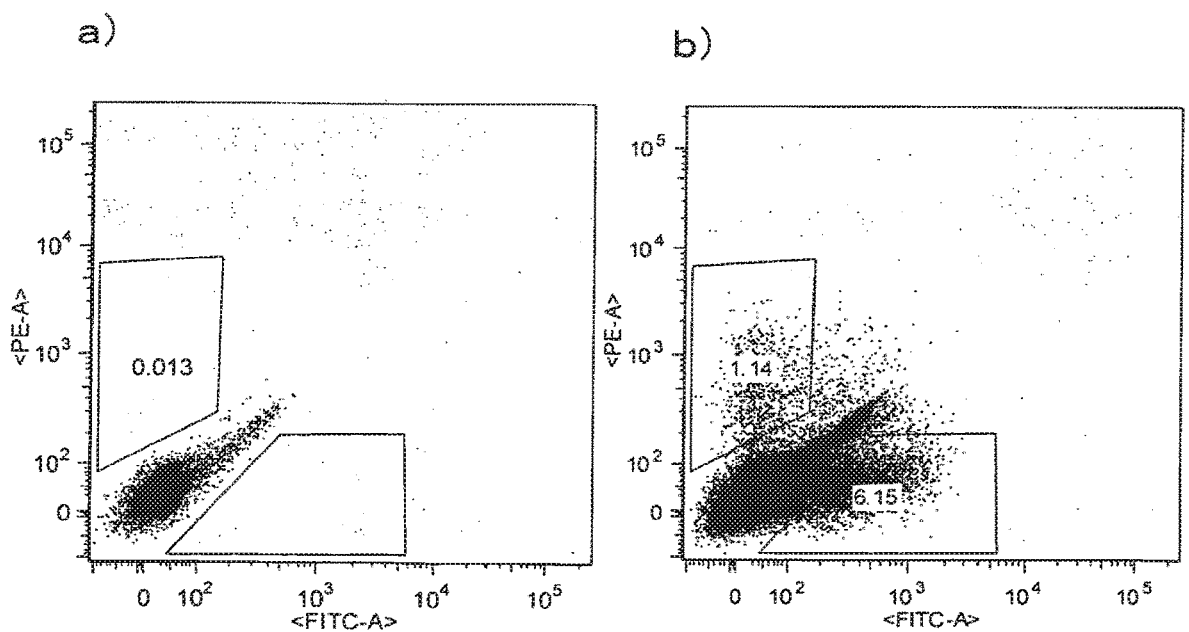
FIG. 4 represents the productions of IFN-γ and IL-17 by HLA-DPB1*0501/*0501-positive mononuclear cells. In the figure, a horizontal axe represents IFN-γ, and a longitudinal axe represents IL-17.

HLA-DPB1*0501/*0501-positive mononuclear cells were used to perform the following experiments. The cells were suspended to X-VIVO (1% AB serum), and 20 μg/ml WT1 peptide, 10 μg/ml Brefeldin A and 0.5 μg/ml CD28/49d were added. They were incubated at 37° C. with 5% $CO_2$ for 4 hours. As a control, a cell incubated without the addition of WT1 peptide was used. After washing with buffer, an anti-CD3-perCP antibody and an anti-CD4-APC antibody were added, and they were incubated at 4° C. for 30 minutes. After washing with buffer, the cells were fixed and permeabilized using a fixation and permeabilization kit BD CYTOFIX/CYTOPERM™ (4° C., 20 minutes). After washing with BD perm/wash buffer, an anti-INF-γ-FITC (BD, clone: B27) and anti-IL-17-PE (eBioscience, clone: eBio64DEC17) were added, and they were incubated at 4° C. for 30 minutes. After washing with buffer, cells were analyzed with FACSAria. The results are shown in FIG. 4. It was confirmed that an HLA-DPB1*0501-positive mononuclear cells grow, and produces IFN-γ and IL-17.

4. Growth Assay

Figure 5:
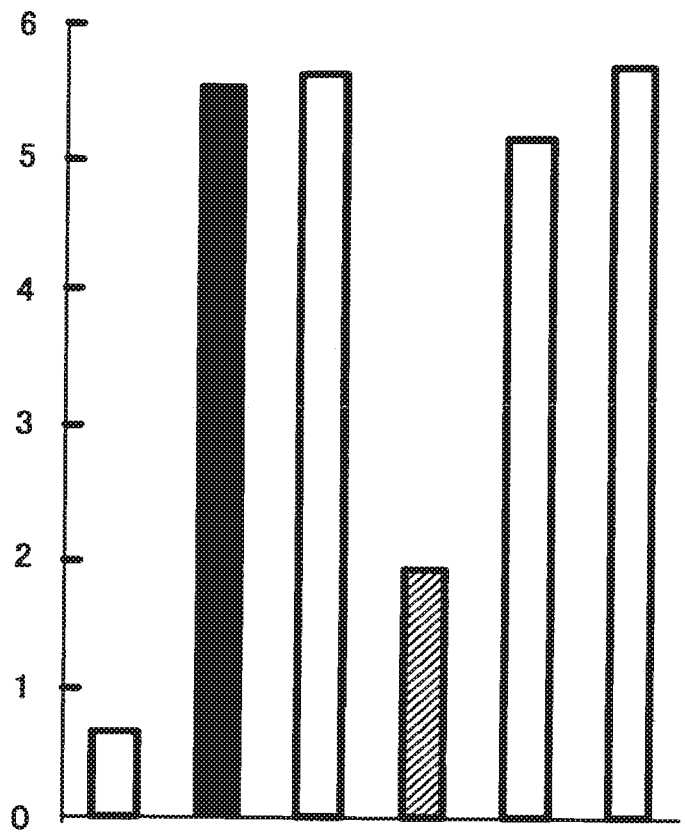
FIG. 5 is a graph which represents the growth of TA28.1 cells. In the figure, a longitudinal axe represents cpm (×10⁴). The graphs correspond to "the case of coculturing TA28.1 cells with peripheral blood mononuclear cells without pulsing with a WT1 peptide", "the case of coculturing TA28.1 cells with peripheral blood mononuclear cells pulsed with a WT1 peptide (black)", "the case of culturing TA28.1 cells with peripheral blood mononuclear cells pulsed with a WT1 peptide in the presence of an anti-MHC class I antibody", "the case of coculturing TA28.1 cells with peripheral blood mononuclear cells pulsed with a WT1 peptide in the presence of an anti-HLA-DR antibody (shaded)", "the case of coculturing TA28.1 cells with peripheral blood mononuclear cells pulsed with a WT1 peptide in the presence of an anti-HLA-DQ antibody", "the case of coculturing TA28.1 cells with peripheral blood mononuclear cells pulsed with a WT1 peptide in the presence of an anti-HLA-Dantibody" starting from the left, respectively.

The growth assay was performed by [³H]-thymidine incorporation method. TA28.1 cells ($3\times10^4$ cells) and peripheral blood mononuclear cells (HLA-DRB1*1501-positive; $1\times10^5$ cells) that had been pulsed with the WT1 peptides and irradiated were cocultured in a 96-well plate. After coculturing for 80 hours, 37 kBq/well [³H]-thymidine (Amersham Biosciences) was added. They were incubated for another 16 hours, and measured using β-scintillation counter. The measurements were represented as count/minute (cpm). As a control, a peripheral blood mononuclear cell without pulsing with a peptide was used. Furthermore, in order to confirm that the activation signal is specific for an HLA-DRB1*1501 molecule, an anti-MHC class I antibody, anti-HLA-DR antibody, anti-HLA-DQ antibody and anti-HLA-DP antibody were used. The results are shown in FIG. 5. It was confirmed that TA28.1 cells were activated by a signal through the WT1 peptide and HLA-DRB1*1501, and grown. It was further confirmed that the growth was specific for HLA-DRB1*1501, because it was suppressed by the anti-HLA-DR antibody.

Figure 6:
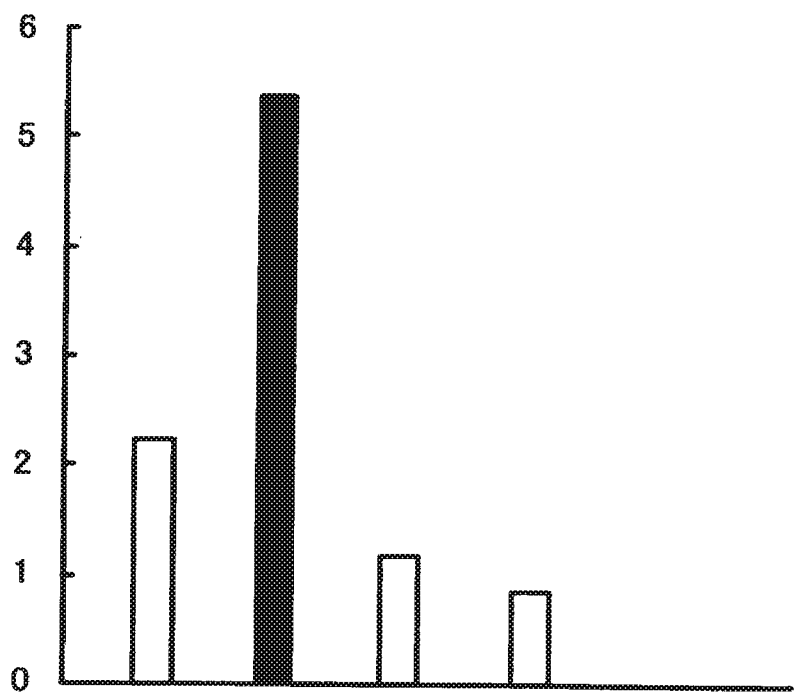
FIG. 6 is a graph which represents the growth of E15.2 cells. In the figure, a longitudinal axe represents cpm (×10⁴). The graphs correspond to "the case of coculturing E15.2 cells with peripheral blood mononuclear cells from an HLA-DPB1*0901-positive subject without pulsing with a WT1 peptide", "the case of coculturing E15.2 cells with peripheral blood mononuclear cells from an HLA-DPB1*0901-positive subject pulsed with a WT1 peptide (black)", "the cases of coculturing E15.2 cells with peripheral blood mononuclear cells from an HLA-DPB1*0901-negative subject without pulsing with a WT1 peptide", "the case of coculturing E15.2 cells with peripheral blood mononuclear cells from an HLA-DPB1*0901-negative subject pulsed with a WT1 peptide" starting from the left, respectively.
Figure 7:
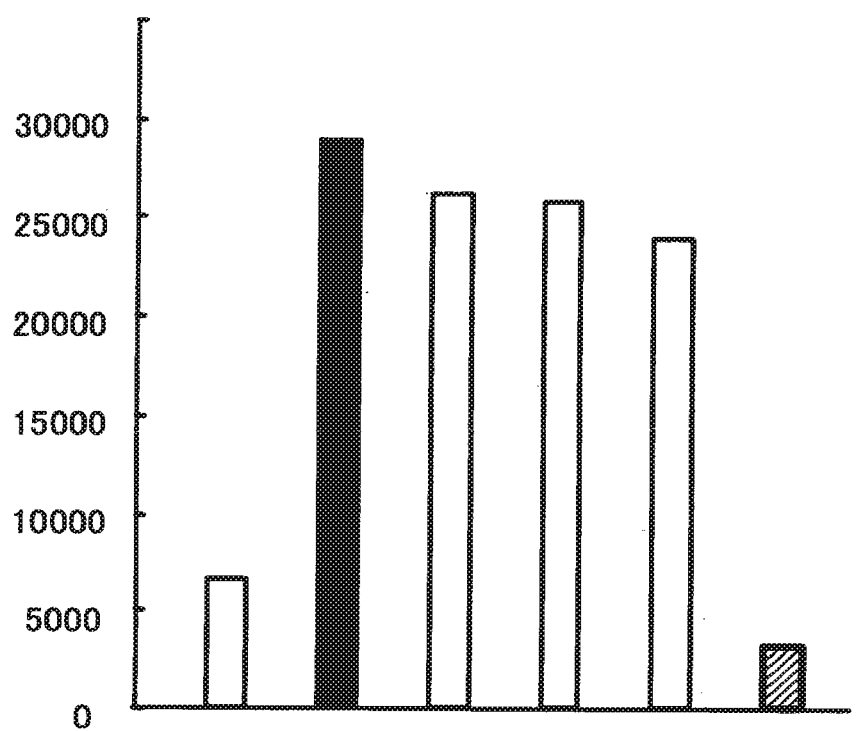
FIG. 7 is a graph which represents the growth of E15.2 cells. In the figure, a longitudinal axe represents cpm. The graphs correspond to "the case of coculturing E15.2 cells with peripheral blood mononuclear cells without pulsing with a WT1 peptide", "the case of coculturing E15.2 cells with peripheral blood mononuclear cells pulsed with a WT1 peptide (black)", "the case of coculturing E15.2 cells with peripheral blood mononuclear cells pulsed with a WT1 peptide in the presence of an anti-MHC class I antibody", "the case of coculturing E15.2 cells with peripheral blood mononuclear cells pulsed with a WT1 peptide in the presence of an anti-HLA-DR antibody", "the case of coculturing E15.2 cells with peripheral blood mononuclear cells pulsed with a WT1 peptide in the presence of an anti-HLA-DQ antibody", and "the case of coculturing E15.2 cells with peripheral blood mononuclear cells pulsed with a WT1 peptide in the presence of an anti-HLA-DP antibody (shaded)" starting from the left, respectively.

Likewise, E15.2 cells were used to perform the growth assay. As an additional control, the peripheral blood mononuclear cells from an HLA-DPB1*0901-negative subject were used. The results are shown in FIGS. 6 and 7. It was confirmed that E15.2 cells were activated by a signal through the WT1 peptide and HLA-DPB1*0901, and grown. It was further confirmed that the growth is specific for HLA-DPB1*0901, because it is suppressed by the anti-HLA-DP antibody.

Figure 8:
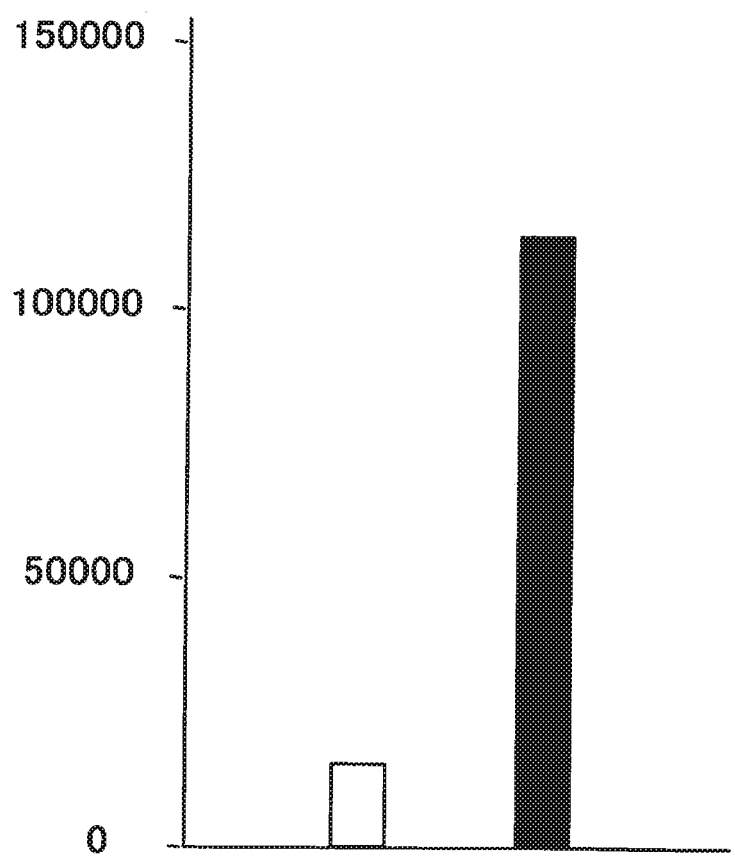
FIG. 8 is a graph which represents the growth of HLA-DPB1*0501/*0501-positive mononuclear cells. In the figure, a longitudinal axe represents cpm. The graphs correspond to "the case without stimulation with a WT1 peptide" and "the case with stimulation with a WT1 peptide" starting from the left, respectively.
Figure 9:
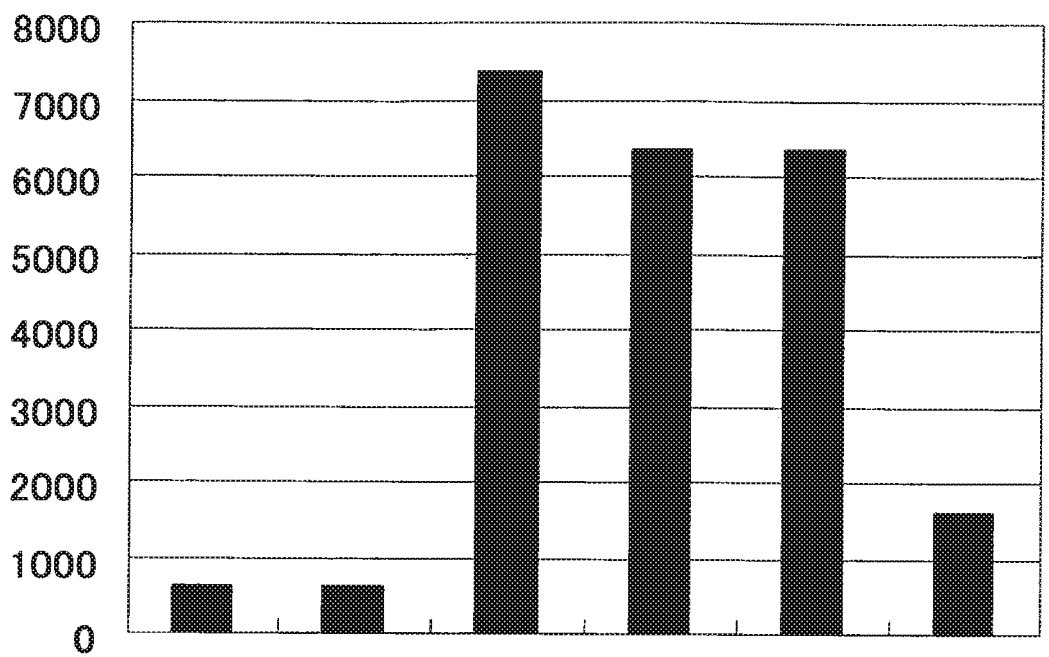
FIG. 9 represents that the growth of HLA-DPB1*0501/*0501-positive mononuclear cells is suppressed by anti-HLA-DP antibodies. In the figure, a longitudinal axe represents cpm. The graphs correspond to "the case without stimulation with a WT1 peptide", "the case with stimulation with a control peptide from HIV", "the case with stimulation with a WT1 peptide", "the case with stimulation with a WT1 peptide in the presence of an anti-HLA-DR antibody", "the case with stimulation with a WT1 peptide in the presence of an anti-HLA-DQ antibody" and "the case with stimulation with a WT1 peptide in the presence of an anti-HLA-Dantibody" starting from the left, respectively.

Furthermore, HLA-DPB1*0501/*0501-positive mononuclear cells were used to perform the growth assay. As a control, a peripheral blood mononuclear cell from an HLA-DPB1*0501-negative subject was also used. The results are shown in FIGS. 8 and 9. It was confirmed that an HLA-DPB1*0501/*0501-positive mononuclear cells were activated by a signal through the WT1 peptide and HLA-DPB1*0501, and grown. It was further confirmed that the growth is specific for HLA-DPB1*0501, because it is suppressed by the anti-HLA-DP antibody.

Figure 10:
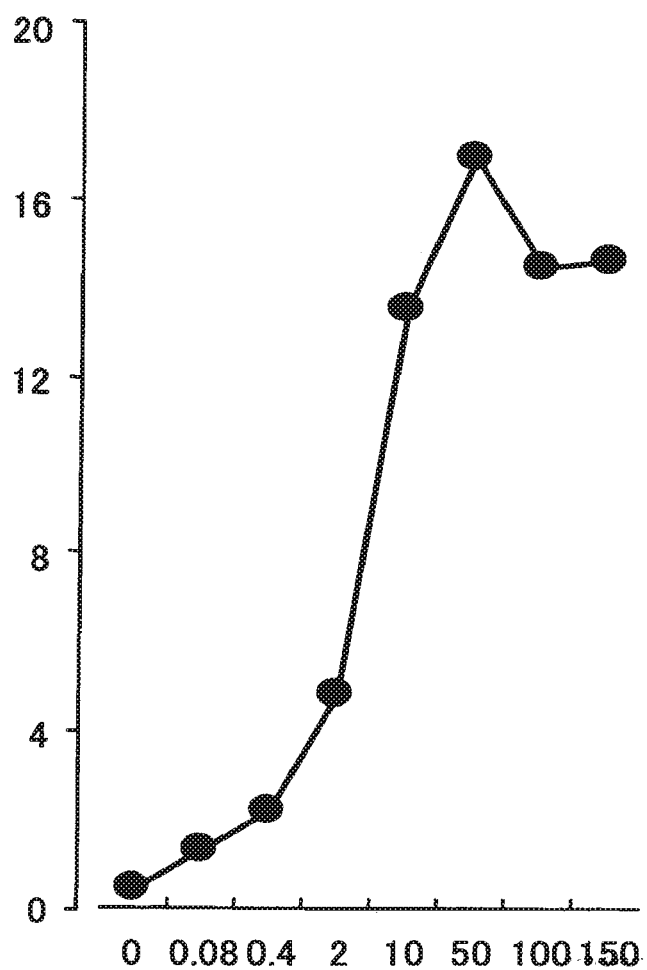
FIG. 10 is a graph which represents the growth of E15.2 cell in the cases of using various concentration of a WT1 peptide. In the figure, a longitudinal axe represents cpm (×10⁴), and a horizontal axe represents the concentration of the WT1 peptide.

Furthermore, the growth assay of the E15.2 cells was performed with various concentrations of the WT1 peptide. The concentration of the used WT1 peptide was 0.08, 0.4, 2, 10, 50, 100 or 150 μg/ml. The results are shown in FIG. 10. It was confirmed that the WT1 peptides grow the E15.2 cells in a concentration-dependent manner.

INDUSTRIAL APPLICABILITY

The present invention provides a method for the activation of a helper T cell with a WT1 peptide which has an ability to bind to an HLA-DRB1*1501 molecule, HLA-DPB1*0901 molecule or HLA-DPB1*0501 molecule and a composition for the same, as well as a pharmaceutical composition for the treatment and/or prevention of a cancer by activating a helper T cell and the like. Therefore, the present invention can be used in the fields of medicine and the like, for example, in the fields of development and preparation of a pharmaceutical composition for the prevention or treatment of various hematopoietic tumors and solid cancers that express WT1 gene at high levels.

The invention claimed is:

1. A method for determining the presence or amount of a WT1-specific helper T cell in a subject positive for an MHC class II molecule selected from the group consisting of HLA-DRB1*1501, HLA-DPB1*0901, and HLA-DPB1*0501, the method comprising:
   (a) obtaining or having obtained a sample from the subject containing an antigen-presenting cell;
   (b) stimulating the sample with a WT1 peptide, thereby generating a complex of the WT1 peptide and the MHC class II molecule that reacts with a helper T cell, if present in the sample; and
   (c) determining the production of a cytokine or the reaction of the helper T cell,
   wherein a presence or an increase in the amount of the production of the cytokine or the reaction of the helper T cell indicates the presence or amount of the WT1-specific helper T cell,
   wherein the WT1 peptide consists of amino acid sequence: Lys Arg Tyr Phe Lys Leu Ser His Leu Gln Met His Ser Arg Lys His (SEQ ID NO:2).

2. The method of claim 1, wherein the subject is also positive for the MHC class II molecule HLA-DRβ1*1502.

* * * * *

SEQUENCE LISTING

```
<160> NUMBER OF SEQ ID NOS: 2

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45
```

```
Gly Ser Leu Gly Gly Pro Ala Pro Pro Ala Pro Pro Pro Pro
    50                  55                  60
Pro Pro Pro His Ser Phe Ile Lys Gln Glu Pro Ser Trp Gly Gly
65              70                  75                  80
Ala Glu Pro His Glu Glu Gln Cys Leu Ser Ala Phe Thr Val His Phe
                85                  90                  95
Ser Gly Gln Phe Thr Gly Thr Ala Gly Ala Cys Arg Tyr Gly Pro Phe
            100                 105                 110
Gly Pro Pro Pro Pro Ser Gln Ala Ser Ser Gly Gln Ala Arg Met Phe
        115                 120                 125
Pro Asn Ala Pro Tyr Leu Pro Ser Cys Leu Glu Ser Gln Pro Ala Ile
    130                 135                 140
Arg Asn Gln Gly Tyr Ser Thr Val Thr Phe Asp Gly Thr Pro Ser Tyr
145                 150                 155                 160
Gly His Thr Pro Ser His His Ala Ala Gln Phe Pro Asn His Ser Phe
                165                 170                 175
Lys His Glu Asp Pro Met Gly Gln Gln Gly Ser Leu Gly Glu Gln Gln
            180                 185                 190
Tyr Ser Val Pro Pro Pro Val Tyr Gly Cys His Thr Pro Thr Asp Ser
        195                 200                 205
Cys Thr Gly Ser Gln Ala Leu Leu Leu Arg Thr Pro Tyr Ser Ser Asp
    210                 215                 220
Asn Leu Tyr Gln Met Thr Ser Gln Leu Glu Cys Met Thr Trp Asn Gln
225                 230                 235                 240
Met Asn Leu Gly Ala Thr Leu Lys Gly Val Ala Ala Gly Ser Ser Ser
                245                 250                 255
Ser Val Lys Trp Thr Glu Gly Gln Ser Asn His Ser Thr Gly Tyr Glu
            260                 265                 270
Ser Asp Asn His Thr Thr Pro Ile Leu Cys Gly Ala Gln Tyr Arg Ile
        275                 280                 285
His Thr His Gly Val Phe Arg Gly Ile Gln Asp Val Arg Arg Val Pro
    290                 295                 300
Gly Val Ala Pro Thr Leu Val Arg Ser Ala Ser Glu Thr Ser Glu Lys
305                 310                 315                 320
Arg Pro Phe Met Cys Ala Tyr Pro Gly Cys Asn Lys Arg Tyr Phe Lys
                325                 330                 335
Leu Ser His Leu Gln Met His Ser Arg Lys His Thr Gly Glu Lys Pro
            340                 345                 350
Tyr Gln Cys Asp Phe Lys Asp Cys Glu Arg Arg Phe Ser Arg Ser Asp
        355                 360                 365
Gln Leu Lys Arg His Gln Arg Arg His Thr Gly Val Lys Pro Phe Gln
    370                 375                 380
Cys Lys Thr Cys Gln Arg Lys Phe Ser Arg Ser Asp His Leu Lys Thr
385                 390                 395                 400
His Thr Arg Thr His Thr Gly Lys Thr Ser Glu Lys Pro Phe Ser Cys
                405                 410                 415
Arg Trp Pro Ser Cys Gln Lys Lys Phe Ala Arg Ser Asp Glu Leu Val
            420                 425                 430
Arg His His Asn Met His Gln Arg Asn Met Thr Lys Leu Gln Leu Ala
        435                 440                 445
Leu
```

```
<210> SEQ ID NO 2
<211> LENGTH: 16
<212> TYPE: PRT
<213> ORGANISM: Homo sapiens

<400> SEQUENCE: 2

Lys Arg Tyr Phe Lys Leu Ser His Leu Gln Met His Ser Arg Lys His
1               5                   10                  15
```